(12) United States Patent
Meyer et al.

(10) Patent No.: US 10,610,505 B2
(45) Date of Patent: *Apr. 7, 2020

(54) CONTROLLED RELEASE DOSAGE FORM

(71) Applicant: OSMOTICA KERESKEDELMI ES SZOLGALTATO KFT, Budapest (HU)

(72) Inventors: Glenn A. Meyer, Wilmington, NC (US); Cristian R. Franco, Buenos Aires (AR); Gustavo A. Fischbein, Buenos Aires (AR); Alejandro A. Aguilar, Buenos Aires (AR); Claude E. Wright, Canton, GA (US)

(73) Assignee: Osmotica Kereskedelmi ES Szolgaltato KFT, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 16/212,093

(22) Filed: Dec. 6, 2018

(65) Prior Publication Data

US 2019/0111013 A1     Apr. 18, 2019

Related U.S. Application Data

(60) Division of application No. 15/680,434, filed on Aug. 18, 2017, now Pat. No. 10,300,032, which is a
(Continued)

(51) Int. Cl.
*A61K 9/28* (2006.01)
*A61K 31/197* (2006.01)
(Continued)

(52) U.S. Cl.
CPC .......... *A61K 31/197* (2013.01); *A61K 9/0004* (2013.01); *A61K 9/0053* (2013.01);
(Continued)

(58) Field of Classification Search
CPC .................................................. A61K 9/2866
See application file for complete search history.

(56) References Cited

U.S. PATENT DOCUMENTS

| 6,340,475 B2 | 1/2002 | Shell |
| 6,488,962 B1 | 12/2002 | Berner |

(Continued)

FOREIGN PATENT DOCUMENTS

| EP | 1849462 A2 | 10/2007 |
| WO | 2005/025559 A1 | 3/2005 |

(Continued)

OTHER PUBLICATIONS

Yang et al. ("Population pharmacokinetics of oral baclofen in pediatric patients with cerebral palsy" in J. Pediatr. (May 2014), 164(5), 1181-1188).
(Continued)

*Primary Examiner* — Benjamin J Packard
(74) *Attorney, Agent, or Firm* — Innovar, L.L.C.; Rick Matos

(57) ABSTRACT

The present invention provides a simple and improved dosage form that is capable of providing a controlled release of $GABA_B$ receptor agonist contained in the core thereof. The invention also provides methods of administering the dosage form and of treating conditions that are therapeutically responsive to $GABA_B$ receptor agonist.

30 Claims, 6 Drawing Sheets

Related U.S. Application Data continuation-in-part of application No. 15/673,985, filed on Aug. 10, 2017, now Pat. No. 10,213,402, which is a continuation of application No. 15/492,714, filed on Apr. 20, 2017, now Pat. No. 9,801,841, which is a continuation of application No. 15/146,525, filed on May 4, 2016, now Pat. No. 9,655,858, which is a continuation of application No. 15/132,972, filed on Apr. 19, 2016, now Pat. No. 9,585,843, which is a continuation of application No. 15/048,743, filed on Feb. 19, 2016, now Pat. No. 9,579,289, said application No. 15/673,985 is a continuation-in-part of application No. PCT/IB2016/000232, filed on Feb. 19, 2016, and a continuation-in-part of application No. PCT/IB2016/000230, filed on Feb. 19, 2016, and a continuation-in-part of application No. PCT/IB2016/000438, filed on Feb. 19, 2016, and a continuation-in-part of application No. PCT/IB2016/000260, filed on Feb. 19, 2016.

(60) Provisional application No. 62/130,757, filed on Mar. 10, 2015, provisional application No. 62/118,910, filed on Feb. 20, 2015, provisional application No. 62/119,017, filed on Feb. 20, 2015, provisional application No. 62/131,495, filed on Mar. 11, 2015.

(51) Int. Cl.
*A61K 9/20* (2006.01)
*A61K 9/00* (2006.01)
*A61K 9/50* (2006.01)
*A61K 9/48* (2006.01)

(52) U.S. Cl.
CPC .......... *A61K 9/2031* (2013.01); *A61K 9/2866* (2013.01); *A61K 9/4866* (2013.01); *A61K 9/5042* (2013.01)

(56) References Cited

U.S. PATENT DOCUMENTS

| | | | |
|---|---|---|---|
| 6,599,284 B2 | 7/2003 | Faour | |
| 6,632,217 B2 | 10/2003 | Harper | |
| 6,923,988 B2 | 8/2005 | Patel | |
| 7,611,728 B2 | 11/2009 | Kidane | |
| 7,736,667 B2 | 6/2010 | Berner | |
| 8,007,827 B2 | 8/2011 | Han | |
| 8,012,496 B2 | 9/2011 | Dudhara | |
| 8,029,822 B2 | 10/2011 | Faour | |
| 8,043,630 B2 | 10/2011 | Berner | |
| 8,143,311 B2 | 3/2012 | Roberts | |
| 8,273,715 B2 | 9/2012 | Roberts | |
| 8,278,276 B2 | 10/2012 | Roberts | |
| 8,329,215 B2 | 12/2012 | Berner | |
| 8,426,470 B2 | 4/2013 | Dudhara | |
| 8,637,080 B2 | 1/2014 | Pastini | |
| 8,703,193 B2 | 4/2014 | Wang | |
| 8,945,619 B2 | 2/2015 | Berner | |
| 9,579,289 B2 | 2/2017 | Meyer | |
| 9,585,843 B2 | 3/2017 | Meyer | |
| 9,655,858 B2 | 5/2017 | Meyer | |
| 9,801,841 B2 | 10/2017 | Meyer | |
| 2005/0090557 A1 | 4/2005 | Devane | |
| 2005/0220873 A1 | 10/2005 | Han | |
| 2005/0226927 A1 | 10/2005 | Han | |
| 2006/0057197 A1 | 3/2006 | Han | |
| 2007/0265343 A1 | 11/2007 | Dharmadhikari | |
| 2008/0206332 A1 | 8/2008 | Kidney | |
| 2009/0041806 A1 | 1/2009 | Cundy | |
| 2009/0118365 A1 | 5/2009 | Benson | |
| 2009/0197958 A1 | 8/2009 | Sastry | |
| 2009/0246233 A1 | 10/2009 | Devane | |
| 2010/0137442 A2 | 6/2010 | Sastry | |
| 2011/0091542 A1 | 4/2011 | Navon | |
| 2011/0200671 A1 | 8/2011 | Dharmadhikari | |
| 2013/0115249 A1 | 5/2013 | Vergez | |
| 2013/0129660 A1 | 5/2013 | Currie | |
| 2013/0237559 A1 | 9/2013 | Ortiz | |
| 2014/0105973 A1 | 4/2014 | Dharmadhikari | |

FOREIGN PATENT DOCUMENTS

| | | |
|---|---|---|
| WO | 2005025559 A1 | 3/2005 |
| WO | 2008/086492 A1 | 7/2008 |
| WO | 2008086492 A1 | 7/2008 |
| WO | 2009/096985 A1 | 8/2009 |
| WO | 2009096985 A1 | 8/2009 |
| WO | 2010/102071 A1 | 9/2010 |
| WO | 2010102071 A1 | 9/2010 |
| WO | 2013/023155 A1 | 2/2013 |
| WO | 2013023155 A1 | 2/2013 |

OTHER PUBLICATIONS

Abdelkader et al. ("Formulation of controlled-release baclofen matrix tablets: Influence of some hydrophilic polymers on the release rate and in vitro evaluation" in AAPS Pharm. Sci. Tech. (Oct. 2007), 8(4), 156).

Vekariya et al. ("Influence of hydrophilic polymers on release profile of baclofen from bilayer tablet" in Int. J. Pharm. Pharm. Sci. (2012), 4(3), 454-458).

Sanchez-Ponce et al. ("Metabolic and Pharmacokinetic Differentiation of STX209 and Racemic Baclofen in Humans" in Metabolites, (2012), 2, 596-613).

Abdelkader et al. ("Formulation of controlled-release baclofen matrix tablets II: Influence of some hydrophilic polymers on the release rate and in vitro evaluation" in AAPS Pharm. Sci. Tech. (Jun. 2008), 9(2), 675-683).

Sampat et al. ("Once daily baclofen sustained release or gastro-retentive system are acceptable alternatives to thrice daily baclofen immediate release at same daily dosage in patients" in Neurol. India (2009), 57(3), 295-299).

Meyer et al. ("CSF and Plasma PK parameters of R-baclofen: Arclofen versus the racemic mixture" in J. Clin. Pharmacol. (Sep. 2011), 51(9), 1351).

Nance et al. ("Efficacy and Safety study of arbaclofen placarbil in patients with spasticity due to spinal cord injury" in Spinal Cord (May 2011), 49(9), 974-980).

Hayek et al. ("Pharmacology of intrathecally administered agents for treatment of spasticity and pain" in Seminars in Pain Medicine, Saunders, US, (Dec. 2003), 1(4), 239).

Meyer et al. ("CSF and Plasma PK Parameters of R-baclofen: Arbaclofen versus the racemic mixture" in J. Clin. Pharm. (2011), 51(9), 1351).

Hayek et al. ("Pharmacology of intrathecally administered agents for treatment of spasticity and pain" in Seminars in Pain Medicine (2003), 1(4), 238-253, Saunders, US).

Nance et al. ("Efficacy and safety study of arbaclofen placarbil in patients with spasticity due to spinal cord injury" in Spinal Cord (2011), 49(9), 974-980).

Rajendra et al. ("Formulation and Evaluation of Controlled Porosity Osmotic Pump Tablets" in Inter. Res. J. Pharm. (2013), 4(5), 181-188).

FIG. 3
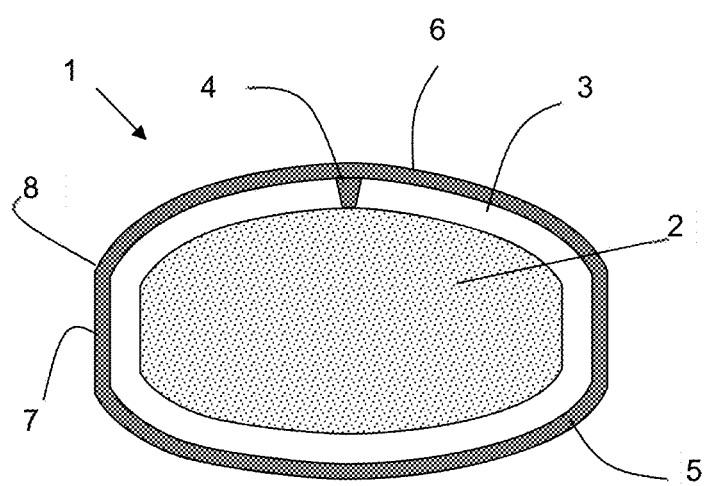
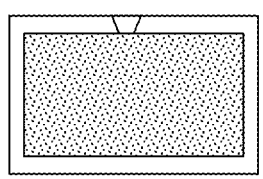
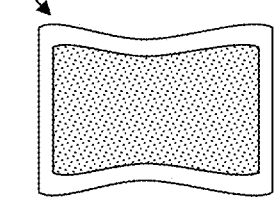

CONTROLLED RELEASE DOSAGE FORM

CROSS-REFERENCE TO EARLIER FILED APPLICATION(S)

This application is a divisional of and claims the benefit of U.S. Ser. No. 15/680,434 filed Aug. 18, 2017, which is a continuation-in-part of U.S. Ser. No. 15/673,985 filed Aug. 10, 2017, which is a continuation of U.S. Ser. No. 15/492,714 filed Apr. 20, 2017, now U.S. Pat. No. 9,801,841 issued Oct. 31, 2017, which is a continuation of U.S. Ser. No. 15/146,525 filed May 4, 2016, now U.S. Pat. No. 9,655,858 issued May 23, 2017, which is a continuation of U.S. Ser. No. 15/132,972 filed Apr. 19, 2016, now U.S. Pat. No. 9,585,843 issued Mar. 7, 2017, which is a continuation of and claims the benefit of U.S. Ser. No. 15/048,743 filed Feb. 19, 2016, now U.S. Pat. No. 9,579,289 issued Feb. 28, 2017, which claims the benefit of provisional application U.S. 62/130,757 filed Mar. 10, 2015, of provisional application U.S. 62/118,910 filed Feb. 20, 2015, of provisional application U.S. 62/119,017 filed Feb. 20, 2015, and of provisional application U.S. 62/131,495 filed Mar. 11, 2015, and the U.S. Ser. No. 15/673,985 application is a continuation-in-part of PCT/IB16/000260 (which is the same as PCT/US16/18767), filed Feb. 19, 2016, and the U.S. Ser. No. 15/673,985 application is a continuation-in-part of PCT/IB16/000232 (which is the same as PCT/US16/18775), filed Feb. 19, 2016, and the U.S. Ser. No. 15/673,985 application is a continuation-in-part of PCT/IB16/000230 (which is the same as PCT/US16/18782), filed Feb. 19, 2016, and the U.S. Ser. No. 15/673,985 application is a continuation-in-part of PCT/IB16/000438 (which is the same as PCT/US16/18786), filed Feb. 19, 2016, the entire disclosures of which are hereby incorporated by reference.

FIELD OF THE INVENTION

This invention pertains to a delivery device for the controlled delivery of arbaclofen to an environment of use. More particularly, it pertains to a controlled release dosage form comprising arbaclofen, wherein the dosage form provides improved efficacy and safety profiles as compared to other dosage forms. In some embodiments, the dosage form provides elevated Cmax and AUC levels on an equivalent dose basis as compared to other controlled release dosage forms. Methods of use thereof are also provided.

BACKGROUND OF THE INVENTION

Spasticity is a common complication in MS (Multiple Sclerosis) and occurs in up to 84% of patients. The main sign of spasticity is resistance to passive limb movement characterized by increased resistance to stretching, clonus, and exaggerated deep reflexes. The associated features of spasticity, including pain, gait disorders, fatigue, and loss of function, significantly affect patient quality of life. Data collected from the North American Research Committee on MS (NARCOMS) Patient Registry showed that 34% of over 20,000 MS patients surveyed experienced moderate, severe, or total limitation of abilities due to spasticity.

Baclofen (racemic baclofen: rac-BAC; (+/−)-4-amino-3-(4-chlorophenyl)-butanoic acid) is a $GABA_B$ receptor agonist that has been used in the United States since 1977 for alleviating the signs and symptoms of spasticity resulting from multiple sclerosis or spinal cord injury. The mechanism of action of baclofen in spasticity appears to involve agonism at $GABA_B$ receptors of the spinal cord (Price et al., Nature 1984, 307(5946), 71-4). Baclofen is believed to inhibit the transmission of both monosynaptic and polysynaptic reflexes at the spinal cord level, possibly by hyperpolarization of primary afferent fiber terminals, with resultant relief of muscle spasticity. Baclofen was approved for marketing as a racemic compound; however, preclinical studies have since demonstrated that the antispasticity activity of the drug resides exclusively in the R-isomer (Albright et al., Neurology, 1995, 45(11), 2110-2111).

The active isomer (R)-baclofen ((L)-baclofen; (−)-baclofen; ARBAC) has also been studied in several clinical trials for the treatment of trigeminal neuralgia, affective disorder, and cerebral spasticity. It has been demonstrated as providing or suggested to provide efficacy in spasticity, spastic diplegia, spasticity associated with multiple sclerosis, amyotrophic lateral sclerosis, trigeminal and glossopharyngeal neuralgias, spinal cord injury, alcoholism, alcohol addiction, dependence or alcohol abuse, gastro-esophageal reflux disease (GERD), emesis, cough, narcotic addiction or abuse, nicotine addiction or abuse, neuropathic pain and musculoskeletal pain, nocturnal acid breakthrough, chronic hiccups, dyspepsia, non-nuclear dyspepsia, gastric motility disorder, migraine, PTSD (Post-traumatic Stress Disorder), depression, anxiety, and lower urinary tract dysfunction.

Baclofen has a number of significant pharmacokinetic limitations including a narrow window of absorption in the upper small intestine and rapid clearance from the blood. Consequently baclofen in immediate release (IR) form is taken three to four times per day to maintain the therapeutic effects. The product literature for LIORESAL® baclofen (an immediate release tablet formulation) indicates doses can be taken in the fed or fasting state with no substantial effect upon pharmacokinetic parameters. There have been no reports in the literature of baclofen (either in racemic or in optically pure or enriched form) exhibiting any positive or negative food effect in any dosage form.

Extended release, sustained release, controlled release and modified release dosage forms containing racemic baclofen (rac-BAC) or (R)-baclofen (ARBAC) are known and reportedly useful for reducing the number of dose administrations per day since they increase the period of drug release and reduce the Cmax as compared to the IR dosage form. Merino et al (Proc. Eur. Congr. Biopharm. Pharmacokinet., $3^{rd}$ (1987), 2, 564-73) describes studies of intestinal absorption of baclofen in the rat small intestine. Merino concludes that administration of sustained-release forms of the drug or the use of increased doses of baclofen to obtain better therapeutic responses may not be suitable for clinical practice in humans.

It would be a significant addition to the art to provide a controlled release dosage form suitable for once or twice daily oral administration that still provides therapeutic levels of ARBAC for an extended period of time without having to increase the dose of ARBAC as compared to repeated doses of an IR dosage form in a day. It would be a further significant addition to the art to provide a controlled release dosage form that provides enhanced bioabsorption of ARBAC on a dose equivalent basis as compared to other controlled release dosage forms.

SUMMARY OF THE INVENTION

The invention provides a controlled release oral dosage form comprising a $GABA_B$ receptor agonist suitable for once or twice daily oral administration to a subject in need thereof for the treatment of a disease, disorder or condition that is therapeutically responsive to the $GABA_B$ receptor agonist. The invention also provides methods of use thereof. The invention provides improved efficacy and safety profiles for drugs when administered as described herein.

The instant dosage form provides enhanced bioabsorption of $GABA_B$ receptor agonist, especially ARBAC, on a dose equivalent basis as compared to other controlled release dosage forms. The combination of drug release profile and composition of the dosage form are such that a majority of the dose of $GABA_B$ receptor agonist in the dosage form is absorbed in a particular region of the GI tract, thereby resulting in improved absorption of the $GABA_B$ receptor agonist.

The present invention overcomes some of the disadvantages of the art by providing a controlled release oral dosage form (AROS or AERT) comprising at least one $GABA_B$ receptor agonist, wherein the dosage form provides an improved clinical benefit over other dosage forms, e.g. over rapid release and over controlled/extended release dosage forms, on a dose equivalent basis. In some embodiments, the dosage form comprises: a) a core comprising at least one $GABA_B$ receptor agonist and at least one excipient, b) a semipermeable membrane surrounding the core and optionally comprising at least one preformed passageway. In some embodiments, the controlled release oral dosage form is an osmotic device.

In some embodiments, the controlled release oral dosage form comprises: a) a core comprising at least one $GABA_B$ receptor agonist and at least one water-swellable excipient, b) a semipermeable membrane surrounding the core and comprising at least one film-forming cellulose ester and optionally at least one preformed passageway.

In each embodiment herein, the presence of the at least one preformed passageway is optional; however, when the preformed passageway is absent, the dosage form ruptures during use.

Some embodiments of the invention those wherein: a) the core comprises at least one $GABA_B$ receptor agonist and at least two water-swellable excipients, and the semipermeable membrane surrounding the core comprises at least two film-forming cellulose esters and optionally at least one preformed passageway; b) the core comprises at least one $GABA_B$ receptor agonist, at least two water-swellable excipients, and at least one osmotic salt, and the semipermeable membrane surrounding the core comprises at least two film-forming cellulose esters and at least one preformed passageway; or c) the core comprises at least one $GABA_B$ receptor agonist, at least two water-swellable excipients, at least one osmotic salt, and at least one binder, and the semipermeable membrane surrounding the core comprises at least two film-forming cellulose esters and at least one preformed passageway.

In some embodiments, the $GABA_B$ receptor agonist: a) is (R)-baclofen (ARBAC); b) excludes (S)-baclofen; c) is not racemic baclofen (rac-BAC); d) is present in salt form; e) is present in freebase form; f) is present in prodrug form; g) excludes a prodrug form; h) excludes a salt form; or i) is a combination of two or more of the above.

In some embodiments, the at least one water-swellable excipient: a) is a water swellable natural, synthetic or semi-synthetic polymer; b) comprises a single grade or type of polymer; c) comprises two different grades of the same type of polymer, meaning the two grades share the same general chemical structure but differ in one or more physical properties; d) comprises two different types of polymer, meaning the two polymers have different general chemical structure and differ in one or more physical properties; e) comprises a combination of a cellulose derivative and poly-alkylene oxide (PAO); f) comprises a combination of hydroxypropyl methylcellulose (HPMC) and polyethylene oxide (PEO); g) comprises a major portion (majority) of a first grade and a minor portion (minority) of a second grade of the same type of polymer; h) comprises a major portion (majority) of a first type and a minor portion (minority) of a second type of polymer; i) comprises a major portion (majority) of PEO and a minor portion (minority) of HPMC; or j) is a combination of two or more of the above.

In some embodiments, the at least one osmotic salt: a) does not have an ion in common with the $GABA_B$ receptor agonist; b) has an ion in common with the $GABA_B$ receptor agonist; c) is a halide salt; or d) is a combination of two or more of the above.

In some embodiments, the film-forming cellulose ester: a) is present as a single type and grade of cellulose ester polymer; b) is present as a combination of at least two different grades of the same type of cellulose ester polymer; c) is present as a combination of two different types of cellulose ester polymer; d) is at least one cellulose acetate polymer; e) is present as at least two different grades of cellulose acetate polymer; f) is present as cellulose acetate Polymer 1 (Grade 1, Grade 3 or combination thereof) and Polymer 2 (Grade 2, Grade 4, Grade 5 or combination thereof); g) has a formulation as described herein; h) is present as a majority of more permeable cellulose acetate polymer (selected from Grade 1 or Grade 3 or a combination thereof as defined herein) and a minority of less permeable cellulose acetate polymer (selected from Grade 2 or Grade 4 or Grade 5 or a combination thereof as defined herein); i) is present as a minority of more permeable cellulose acetate polymer (selected from Grade 1 or Grade 3 or a combination thereof as defined herein) and a majority of less permeable cellulose acetate polymer (selected from Grade 2 or Grade 4 or Grade 5 or a combination thereof as defined herein); or j) is a combination of two or more of the above.

The invention includes embodiments wherein the formulations for the dosage form detailed in Examples 1, 2, 9, 11, 12 and 14 are generalized such that different combinations of the core formulations and membrane formulations in the examples are used.

In some embodiments, the semipermeable membrane does not rupture during use of the dosage form, within 24 hours after administration of the dosage form to a subject or within 24 hours after placement in an aqueous environment of use. In other embodiments, the semipermeable membrane ruptures during use of the dosage form, within about 0.1 to about 2 hours, about 0.1 to about 1.5 hours, about 0.1 to about 1 hour, about 0.1 to about 0.75 hours or about 0.1 to about 0.5 hours after administration of the dosage form to a subject or after placement in an aqueous environment of use. When the membrane ruptures, it forms at least one rupture-formed passageway, which is spaced away from the preformed passageway(s) (if present). The at least one rupture-formed passageway can be formed in the membrane adjacent or along an edge or seam on the surface of the core.

In some embodiments, the core: a) further comprises at least one binder; b) further comprises at least one filler; c) further comprises at least one antioxidant; d) further comprises at least one glidant; e) further comprises at least one lubricant; f) comprises about 5 to about 25 mg, about 5 to about 13 mg, about 13 to about 17 mg, about 17 to about 25 mg, about 5 mg, about 10 mg, about 15 mg, about 20 mg or about 25 mg of $GABA_B$ receptor agonist; g) has a formulation as described herein; h) is a unitary core (non-layered construction); h) comprises a mixture of ingredients; i) is a compressed composition; j) excludes a composition or coat or layer between the core and the semipermeable membrane; or k) is a combination of two or more of the above.

In some embodiments, the dosage form: a) provides a controlled release of $GABA_B$ receptor agonist for a period of at least 8, at least 10, at least 12, at least 16, at least 20 and/or up to 24 hours after administration; b) provides a release of $GABA_B$ receptor agonist characterized by an in vitro sigmoidal dissolution profile determined as described herein; c) provides a plasma profile defined by the pharmacokinetic parameters described herein; d) exhibits a positive food effect in terms of bioavailability, Tmax, Cmax, $AUC_{0-t}$ and/or $AUC_{0-inf}$ when comparing oral administration of the dosage form in the fed and fasting states; and/or e) further comprises an immediate or rapid release composition comprising $GABA_B$ receptor agonist.

In some embodiments, the dosage form: a) comprises a drug-containing coat exterior to the semipermeable membrane; b) comprises an inert water soluble or erodible coat composition surrounding the semipermeable membrane and between the semipermeable membrane and another coat; c) comprises one or more compression coatings and one or more sprayed-on coatings or membranes exterior to the semipermeable membrane; d) excludes a drug-containing coat exterior to the semipermeable membrane; e) comprises an inert water soluble or erodible coat external to the semipermeable membrane; or f) comprises at least any two of the above The present invention further provides a method for treating a condition, disorder or disease that is therapeutically responsive to ARBAC, the method comprising administering a controlled release dosage form as described herein. In some embodiments, the condition, disease or disorder is selected from the group consisting of trigeminal neuralgia, affective disorder, cerebral spasticity, spasticity, spastic diplegia, multiple sclerosis, spasticity associated with multiple sclerosis, amyotrophic lateral sclerosis, trigeminal and glossopharyngeal neuralgias, spinal cord injury, alcoholism, alcohol addiction, dependence or alcohol abuse, gastroesophageal reflux disease (GERD), emesis, cough, narcotic addiction or abuse, nicotine addiction or abuse, neuropathic pain and musculoskeletal pain, nocturnal acid breakthrough, chronic hiccups, dyspepsia, non-nuclear dyspepsia, gastric motility disorder, migraine, PTSD (Post-traumatic Stress Disorder), depression, anxiety, and lower urinary tract dysfunction.

In some aspects, the dosage form of the invention exhibits a substantial positive food effect, whereby it provides an increased Cmax and AUC when administered orally in the fed state as compared to the fasting state. The positive food effect can be used to alter the dosing regimen of the dosage form. In some embodiments, the invention provides a method of administering ARBAC to a subject in need thereof, the method comprising: a) orally administering a first dose of an extended release dosage form of the invention in the fed state, and b) orally administering a second dose of an extended release dosage form of the invention in the fasting state.

In some embodiments, the dosage form provides a majority of drug release in the upper portion of the GI tract following oral administration. In some embodiments, a majority of the drug is released in the small intestine, or a majority of the drug is released at least in the duodenum and jejunum.

In some embodiments, the invention provides a method of administering ARBAC to a subject in need thereof, the method comprising: a) orally administering a first dose of ARBAC in an extended release dosage form of the invention in the fed state, and b) orally administering a second dose of ARBAC in an extended release dosage form of the invention in the fasting state, wherein the first and second doses are administered about 8 to about 16 hours apart.

In some embodiments, the invention provides a method of administering ARBAC to a subject in need thereof, the method comprising: a) orally administering a first dose of ARBAC in an extended release dosage form in the fed state, and b) orally administering a second dose of ARBAC in an extended release dosage form in the fasting state, wherein at least one of the dosage forms exhibits a substantial positive food effect.

In some embodiments, the invention provides a method of administering ARBAC to a subject in need thereof, the method comprising: a) orally administering a first dose of ARBAC in an extended release dosage form in the fed state, and b) orally administering a second dose of ARBAC in an extended release dosage form in the fasting state, wherein the first and second dosage forms are the same and exhibit a substantial positive food effect.

In some embodiments, the invention provides a method of administering ARBAC to a subject in need thereof, the method comprising: a) orally administering a first dose of ARBAC in an extended release dosage form in the fed state, and b) orally administering a second dose of ARBAC in an extended release dosage form in the fasting state, wherein the first and second dosage form are the same and exhibit a substantial positive food effect, and the first and second doses are administered about 8 to about 16 hours apart.

In some embodiments, the invention provides a method of administering ARBAC to a subject in need thereof, the method comprising: a) orally administering a first dose of ARBAC in a first extended release dosage form in the fed state, and b) orally administering a second dose of ARBAC in a second extended release dosage form in the fasting state, wherein the first and second dosage forms comprise different doses of ARBAC, the first dosage form exhibits a substantial positive food effect, and the first and second doses are administered about 8 to about 16 hours apart.

In some embodiments, the invention provides a method of administering ARBAC to a subject in need thereof, the method comprising: a) orally administering a first dose of ARBAC in an extended release dosage form in the fed state, and b) orally administering a second dose of ARBAC in an extended release dosage form in the fasting state, wherein: a) the first and second dosage form are the same and exhibit a substantial positive food effect; and b) the first dose is greater than the second dose. In some embodiments, the first dose is at least 1.2-fold, at least 1.5-fold, at least 1.75-fold or at least 2-fold greater than the second dose.

In some embodiments, the invention provides a method of administering ARBAC to a subject in need thereof, the method comprising: a) orally administering a first dose of ARBAC in an extended release dosage form in the fed state, and b) orally administering a second dose of ARBAC in an extended release dosage form in the fasting state, wherein: a) the first and second dosage form are the same and exhibit a substantial positive food effect; and b) the first dose is lower than the second dose. In some embodiments, the first dose is at least 1.2-fold, at least 1.5-fold, at least 1.75-fold or at least 2-fold lower than the second dose.

The extended release dosage form comprises a dose of ARBAC. In some embodiments, the extended release dosage form exhibits a substantial positive food effect. In some embodiments, the dosage form exhibits enhanced pharmacokinetics as compared to other controlled release dosage forms. In some embodiments, the extended release dosage form provides about the same or greater Cmax and about the same or greater AUC as compared to oral administration of a reference immediate release dosage form comprising the same dose of ARBAC (GABA$_B$ receptor agonist) and still provides substantially the same or an improved clinical benefit over the immediate release dosage form. In some embodiments, the extended release dosage form provides about the same Cmax and a greater AUC as compared to oral administration of a reference immediate release dosage form comprising the same dose of ARBAC (GABA$_B$ receptor agonist) and still provides substantially the same or an improved clinical benefit over the immediate release dosage form. In some embodiments, the extended release dosage form provides a greater Cmax and about the same AUC as compared to oral administration of a reference immediate release dosage form comprising the same dose of ARBAC (GABA$_B$ receptor agonist) and still provides substantially the same or an improved clinical benefit over the immediate release dosage form. In some embodiments, the extended release dosage form provides a greater Cmax and a greater AUC as compared to oral administration of a reference immediate release dosage form comprising the same dose of ARBAC (GABA$_B$ receptor agonist) and still provides substantially the same or an improved clinical benefit over the immediate release dosage form. In some embodiments, the dosage form exhibits a Tmax in the range of 4.5 to 5.5 hours.

In some embodiments, the first dose is administered during the first 12-hour period of a 24-hour period and the second dose is administered during the second 12-hr period of the same 24-hour period. In some embodiments, the first dose is administered during the second 12-hour period of a 24-hour period and the second dose is administered during the first 12-hr period of the same 24-hour period. In some embodiments, the first and second doses are administered about 8 to about 16 hours, about 9 to about 15, about 10 to about 14, about 11 to about 13 or about 12 hours apart. In some embodiments, the first dose is administered in the morning hours, and the second dose is administered in the evening or nighttime hours. In some embodiments, the first dose is administered in the evening or nighttime hours, and the second dose is administered in the morning hours. In some embodiments, the first dose is approximate twice the amount of the second dose. In some embodiments, the method of the invention is repeated daily.

The order of administration of the first dose and second dose can be reversed as desired in any embodiment of the invention.

Another aspect of the invention provides a method of changing the current method of treatment of a subject undergoing daily treatment with one or more ARBAC (or GABA$_B$ receptor agonist) or rac-BAC (or racemic GABA$_B$ receptor agonist) doses to a second method of treatment, the second method of treatment comprising: administering ARBAC to the subject according to one or more of the methods described herein.

In some embodiments, the second method of treatment comprises: a) orally administering a first dose of an extended release dosage form of ARBAC in the fed state, and b) orally administering a second dose of an extended release dosage form of ARBAC in the fasting state.

The positive food effect of the extended release dosage form of the invention can be used to advantage by allowing administration of lower doses of ARBAC (GABA$_B$ receptor agonist) as compared to rac-BAC (racemic GABA$_B$ receptor agonist) while providing substantially the same or even improved clinical benefit. In some embodiments, the invention provides a method of changing the current method of treatment of a subject currently undergoing daily treatment with one or more rac-BAC daily doses to a second method of treatment, the method comprising: a) determining the current daily dose of rac-BAC in the subject's current method of treatment; and b) if the subject is currently taking rac-BAC, indicating administration of a different dose of ARBAC (GABA$_B$ receptor agonist) in an extended release dosage form under fed conditions as the second method, wherein the different daily dose is less than the current daily dose. In some embodiments, the different daily dose is less than 50 by wt % or mole %, on the basis of ARBAC, of the current daily dose. In some embodiments, the second method provides about the same clinical benefit as or provides an improved clinical benefit over the first (current) method. In some embodiments, the second method employs less than 50% of the dose of ARBAC as compared to the first (current) method.

In some embodiments, the subject's current method of treatment is ceased before initiating the second method of treatment. In some embodiments, the subject's current method of treatment and the second method of treatment according to the invention overlap. In some embodiments, the subject's current method of treatment comprises oral, intrathecal, intravenous, intramuscular or intraperitoneal administration of ARBAC or rac-BAC. In some embodiments, the current method of treatment employs immediate release oral dosage forms.

The invention also provides a method of increasing the concentration of ARBAC in the cerebrospinal spinal fluid (CSF) of a subject, the method comprising: a) administering a first total daily dose of ARBAC or rac-BAC to the subject for a period of at least two days sufficient to achieve at least a minimum therapeutically effective concentration of ARBAC in the CSF for a period of at least 12, at least 16 hours, at least 20 hours or at least 24 hours after administration within a 24-hour dosing period; and b) chronically orally administering second total daily doses of ARBAC in an extended or controlled release dosage form to the subject throughout a treatment period sufficient to maintain the at least minimum therapeutically effective concentration of ARBAC in the CSF for a period of at least 16 hours, at least 20 hours or at least 24 hours on a steady state basis within a 24-hour dosing period.

The invention includes embodiments, wherein: a) the first total daily dose is higher than the second total daily dose; b) the first total daily dose is lower than the second total daily dose; c) the minimum therapeutically effective concentration of ARBAC in the CSF is at least about 2, at least about 3 or at least about 4 ng/ml when a total daily dose of 20 mg of ARBAC or a total daily dose of rac-BAC is administered; d) the minimum therapeutically effective concentration of ARBAC in the CSF is at least about 3, at least about 4 or at least about 5 ng/ml when a total daily dose of 30 mg of ARBAC or a total daily dose of rac-BAC is administered; and/or e) the minimum therapeutically effective concentration of ARBAC in the CSF is at least about 5, at least about 6 or at least about 7 ng/ml when a total daily dose of 40 mg of ARBAC or a total daily dose of rac-BAC is administered.

In some embodiments, the extended or controlled release dosage form of the invention provides a Cmax and AUC for ARBAC that is lower than that provided by an immediate release dosage form comprising rac-BAC but the same molar amount of (R)-BAC and still provides substantially the same or an improved clinical benefit over the immediate release dosage form.

In some embodiments, the extended or controlled release dosage form of the invention provides a lower Cmax and about the same AUC for ARBAC as that provided by an immediate release dosage form comprising rac-BAC but the same molar amount of (R)-BAC and still provides substantially the same or an improved clinical benefit over the immediate release dosage form.

The invention provides a method of treating spasticity in a subject having multiple sclerosis comprising orally administering one or more AERT's, wherein the AERT is at least as therapeutically effective as but with less adverse events than treatment with rapid release tablets racemic baclofen on an equimolar basis of arbaclofen. The AERT of the invention provides reduced adverse events than immediate release tablet on an equimolar arbaclofen basis.

The invention provides a method of treating a condition that is therapeutically responsive to arbaclofen comprising orally administering one or more AERT's to a subject in need thereof, wherein the method provides reduced adverse events associated with baclofen therapy. The invention also provides use of AERT's for the treatment of a condition that is therapeutically responsive to arbaclofen comprising administering one or more AERT's as described herein to a subject in need thereof according to a dosing regimen as described herein.

The dosage form of the invention is administered orally once, twice or three-times daily, including daytime and/or nighttime administration.

In some embodiments, the dosage form of the invention releases a majority of arbaclofen downstream of the stomach and upstream of the colon.

The invention provides a method of administering arbaclofen at a reduced dose while maintaining therapeutic efficacy and reducing adverse events, the method comprising orally administering a daily dose of arbaclofen in one or more dosage forms of the invention to a subject in need thereof, wherein the daily dose of the dosage form of the invention comprises a lower daily dose of arbaclofen than that of a reference immediate release dosage form, and the dosage form of the invention is at least as or more therapeutically effective as the reference IR dosage form and provides reduced adverse events as compared to the IR dosage form.

The invention provides a method of treating a condition that is therapeutically responsive to arbaclofen, the method comprising orally administering to a subject a daily dose of arbaclofen in one or more dosage forms of the invention, wherein the daily dose is less than that which would be administered to the subject in an immediate release dosage form and wherein the one or more dosage forms of the invention are at least as or more therapeutically effective and provide less adverse events than the immediate release dosage form.

In some embodiments, the invention provides a controlled or extended release dosage form comprising arbaclofen, wherein following oral administration the dosage form provides a higher $AUC_{0\text{-}inf}$ and higher Cmax and a longer Tmax than that provided by an immediate release capsule containing the same amount of arbaclofen. The dosage form can have an in vitro dissolution profile approximately as described in FIG. 6 and can have an in vivo single dose plasma profile approximately as described in FIG. 7.

In some embodiments, the invention provides a controlled or extended release dosage form comprising arbaclofen, wherein following oral administration the dosage form provides an $AUC_{0\text{-}inf}$ and a Cmax that are at least the same as or higher than the $AUC_{0\text{-}inf}$ and Cmax, respectively, provided by an immediate release capsule containing the same amount of arbaclofen and a longer Tmax than that provided by the immediate release capsule.

In some embodiments, the dosage form exhibits enhanced pharmacokinetics as compared to other controlled release dosage forms. In some embodiments, the extended release dosage form provides about the same or greater Cmax and about the same or greater AUC as compared to oral administration of a reference immediate release dosage form comprising the same dose of ARBAC ($GABA_B$ receptor agonist) and still provides substantially the same or an improved clinical benefit over the immediate release dosage form. In some embodiments, the extended release dosage form provides about the same Cmax and a greater AUC as compared to oral administration of a reference immediate release dosage form comprising the same dose of ARBAC ($GABA_B$ receptor agonist) and still provides substantially the same or an improved clinical benefit over the immediate release dosage form. In some embodiments, the extended release dosage form provides a greater Cmax and about the same AUC as compared to oral administration of a reference immediate release dosage form comprising the same dose of ARBAC ($GABA_B$ receptor agonist) and still provides substantially the same or an improved clinical benefit over the immediate release dosage form. In some embodiments, the extended release dosage form provides a greater Cmax and a greater AUC as compared to oral administration of a reference immediate release dosage form comprising the same dose of ARBAC ($GABA_B$ receptor agonist) and still provides substantially the same or an improved clinical benefit over the immediate release dosage form. In some embodiments, the dosage form exhibits a Tmax in the range of 4.5 to 5.5 hours.

The invention provides a method of treating a condition that is therapeutically responsive to arbaclofen by orally administering the controlled or extended release dosage forms described herein.

The invention includes all combinations of the aspects, embodiments and sub-embodiments disclosed herein. Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIGS. 3 and 4A-4B depict sectional side views of exemplary controlled release dosage forms according to the invention.

DETAILED DESCRIPTION OF THE INVENTION

Figure 1:
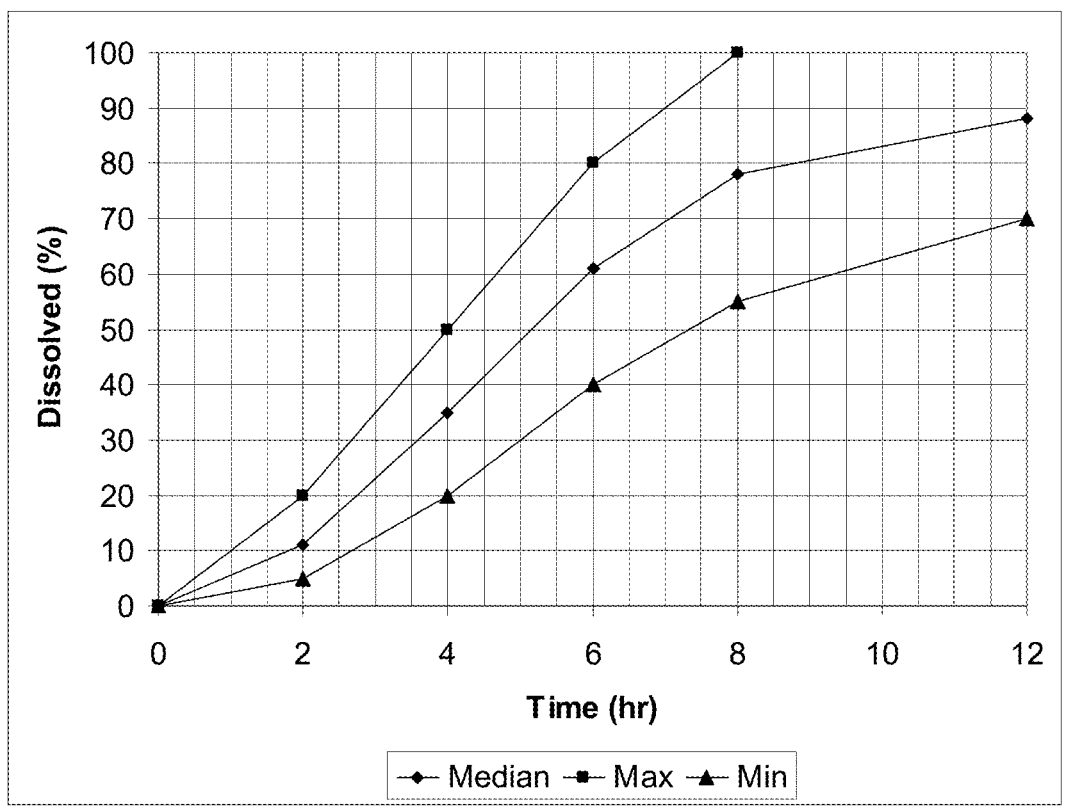
FIG. 1 depicts exemplary in vitro release profiles (max: squares; median: diamonds; min: triangles) for the controlled release device according to Example 1.

By "environment" is meant an "environment of use", which is a locale in which a device of the invention is placed and into which the contents of the device (dosage form) are released. By "aqueous environment of use" is meant an environment of use containing an aqueous medium to which a device of the invention is exposed during use. The aqueous medium can be water, buffer, aqueous fluid, body fluid or other such medium. Exemplary aqueous environments of use include a subject, an assay fluid, or other similar environments. A subject can be human or non-human.

By "rapid release" is meant a release of an active agent to an environment over a period of 1-59 minutes or 1 minute to three hours once release has begun and release can begin within a few minutes after administration or after expiration of a delay period (lag time) after administration.

By "immediate release" is meant a release of an active agent to an environment over a period of seconds to no more than about 30 minutes once release has begun and release begins within a second to no more than about 15 minutes after administration. An immediate release dosage form is considered a more narrowly defined rapid release dosage form, so the terms may be used interchangeably herein.

By "controlled release" is meant a release of an active agent to an environment over a period of about eight hours up to about 12 hours, up to about 14 hours, up to about 16 hours, up to about 18 hours, up to about 20 hours, a day, or more than a day. The terms controlled release, sustained release and extended release are used interchangeably herein. A controlled release can also mean substantially continuous release of drug throughout the majority of the transit time of the dosage form through the gastrointestinal tract following oral administration thereof.

A controlled release can begin within a few minutes after administration or after expiration of a delay period (lag time) after administration.

A delayed but controlled release dosage form is one that provides a delayed release of a drug followed by a controlled release of the drug. By delayed release is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, 30 minutes to 10 hours, 15 min to 5 hours, 15 min to 2 hours, 15 min to 1 hour, or 1 hour to 10 hours.

A zero-order release profile characterizes the release profile of a dosage form that releases a constant amount of drug per unit time. A pseudo-zero order release profile is one that approximates a zero-order release profile. A dissolution curve shows a zero or pseudo-zero order release profile if its release rate remains constant (or relatively constant within ±10% of the average value) in the interval of time $0 \le a < t \le b$. Any profile following the equation:

$$(M(t)/M_r) = k(t-a)^n \quad 0.9 \le n \le 1.1$$

has the following release rate equation:

$$(1/M)(dM/dt) = kn(t-a)^{n-1}$$

A first order release profile characterizes the release profile of a dosage form that releases a percentage of a drug charge per unit time. A pseudo-first order release profile is one that approximates a first order release profile. A dissolution curve shows a first or pseudo-first order release profile within a certain interval of time $0 \le a < t \le b$ if its release rate is a continued monotone decreasing function of time. Specifically, a dissolution curve shows a first order profile whenever its release rate is proportional to the remaining undissolved amount of drug, as determined by the following equation:

$$(M(t)/MT) = 1 - \exp(-kt)$$

A dissolution curve shows a pseudo-first order profile when the drug release rate decreases with time as described by the Fickian or anomalous Fickian diffusion controlled release equation:

$$(M(t)/M_T) = kt^n, 0.3 \le n \le 0.7$$

In some embodiments, the invention excludes dosage forms that exhibit a zero order or first order release profile.

A sigmoidal release profile characterizes the release profile of a dosage form that releases a drug in a controlled manner but very slowly during a first release period, then more rapidly during a second release period and finally very slowly during a third release period such that the release profile resembles a sigmoid. A dissolution curve shows a sigmoid release profile within a certain interval of time $0 \le a < t \le b$ if its release rate reaches a single maximum within the interval (a, b) excluding the extremes. That is equivalent to consider a point of time T* so that the release rate is an increasing function of time for $a \le t < T^*$ and a decreasing function of time, as determined by the following equation: Weibull Function $$(M(t)/M_T) = W_{inf}\{1 - \exp\{-[(t-t_i)/\beta]^\alpha\}\} \text{ Parameter ranges:}$$

$t_i$: between 0 and 3
$\beta$: between 7 and 12
$\alpha$: $1 < \alpha < 3$
Winf: between 0.5 and 1.1

The core comprises at least one and preferably at least two water swellable excipients which expand in size during use of the dosage form. A gel or gelatinous mass forms in the core when exposed to water. Drug is extruded from the core in the form of a gel via the preformed passageway and/or the passageway formed by rupture. The drug diffuses from the gel in dissolved form during use.

In some embodiments, the dosage form exhibits a sigmoidal drug release (dissolution) profile. A sigmoidal release profile can be divided into three phases: a first slower release rate phase, a second faster release rate phase and a third slower release rate phase. An exemplary release profile can be characterized as follows and as depicted in FIG. 1.

TABLE 1

| Time (hr) | Dissolution (% wt) | | |
| --- | --- | --- | --- |
| | Median or mean | Max | Min |
| 0 | 0 | 0 | 0 |
| 2 | 11 | 20 | 5 |
| 4 | 35 | 50 | 20 |
| 6 | 61 | 80 | 40 |
| 8 | 78 | 100 | 55 |
| 12 | 88 | | 70 |

TABLE 2

| Time (hr) | Dissolution (% wt) | | |
|---|---|---|---|
| | Median or mean | Max | Min |
| 0 | 0 | 0 | 0 |
| 2 | 11 | 20 | 5 |
| 4 | 35 | 50 | 25 |
| 6 | 61 | 80 | 45 |
| 8 | 78 | 100 | 65 |
| 12 | 88 | | 80 |

TABLE 3

| Time (hr) | Dissolution (% wt) | | |
|---|---|---|---|
| | Median or mean | Max | Min |
| 0 | 0 | 0 | 0 |
| 2 | 12 | 20 | 5 |
| 4 | 40 | 50 | 30 |
| 6 | 65 | 80 | 50 |
| 8 | 85 | 100 | 70 |
| 12 | 95 | | 90 |

TABLE 4

| Time (hr) | Dissolution (% wt) | | |
|---|---|---|---|
| | Median or mean | Max | Min |
| 0 | 0 | 0 | 0 |
| 2 | 12 | 20 | 5 |
| 4 | 42 | 50 | 35 |
| 6 | 67 | 80 | 55 |
| 8 | 87 | 100 | 75 |
| 12 | 97 | | 100 |

TABLE 5

| Time (hr) | Dissolution (% wt) | | |
|---|---|---|---|
| | Median or mean | Max | Min |
| 0 | 0 | 0 | 0 |
| 1 | 11 | 15 | 5 |
| 2 | 20 | 30 | 11 |
| 4 | 50 | 72 | 35 |
| 6 | 80 | 100 | 61 |
| 8 | 100 | | 78 |

TABLE 6

| Time (hr) | Dissolution (% wt) | | |
|---|---|---|---|
| | Median or mean | Max | Min |
| 0 | 0 | 0 | 0 |
| 1 | 7 | 10 | 2 |
| 2 | 15 | 20 | 7 |
| 4 | 40 | 50 | 25 |
| 6 | 65 | 85 | 50 |
| 8 | 85 | 100 | 70 |
| 10 | 100 | | |

The values set forth in the above tables and herein are approximate numbers. Depending upon the conditions of measurement as well as the assay used to determine those values, they may have a standard deviation of +/−2%, +/−5% or +/−10% of the indicated value.

The maximum and minimum release profiles can be thought of as approximations of the upper and lower boundaries within which the release profile of the exemplary osmotic device will vary on an overall or point to point basis. In other words, the area defined by the upper and lower boundaries is an approximation of the mean release profile plus or minus the standard deviation at the points of measurement. Other methods of forming an edge or seam on the surface of the osmotic device before application of the film-forming material are considered within the scope of the invention.

The dosage form of the invention can provide a release profile wherein about 40 to about 100% wt of the drug is released in a controlled or continuous manner over a period of about 6 to about 16 hours, about 6 to about 14 hours, about 6 to about 12 hours, about 6 to about 10 hours, about 6 to about 9 hours, about 6 to about 8 hours, about 7 to about 14 hours, about 8 to about 14 hours, or about 10 to about 14 hours after placement in an environment of use or after oral administration.

The release can be such that about 40 to about 80% wt of the drug is released by about six hours, about 55 to about 100% of the drug is released by about 8 hours, and no less than 70% of the drug is released by about 12 hours after placement in an environment of use or after oral administration.

The release can be such that about 50 to about 100% wt of the drug is released by about six hours, about 65 to about 100% of the drug is released by about 8 hours, and no less than 90% of the drug is released by about 12 hours after placement in an environment of use or after oral administration.

The release can be such that about 60 to about 100% wt of the drug is released by about six hours, about 75 to about 100% of the drug is released by about 8 hours, and no less than 90% of the drug is released by about 10 hours after placement in an environment of use or after oral administration.

The release can also be such that about 45 to about 85% wt of the drug is released by six hours, about 65 to about 100% of the drug is released by 8 hours, and no less than 75% of the drug is released by 12 hours. The release can also be such that about 50 to about 85% wt of the drug is released by six hours, about 70 to about 100% of the drug is released by 8 hours, and no less than 85% of the drug is released by 10 hours. The release can also be such that about 5 to about 40% wt of the drug is released by 2 hours, 45 to about 85% wt of the drug is released by six hours, about 65 to about 100% of the drug is released by 8 hours, and no less than 75% of the drug is released by 12 hours.

The release can also be such that about 10 to about 20% wt of the drug is released by 2 hours, about 25 to about 50% is released by 4 hours, about 60 to about 90% wt of the drug is released by 8 hours, and no less than 75% of the drug is released by 12 hours. The release can also be such that about 10 to about 20% wt of the drug is released by 2 hours, about 25 to about 50% is released by 4 hours, 60 to about 90% wt of the drug is released by 8 hours, and no less than 80% of the drug is released by 12 hours. The release can also be such that about 7 to about 20% wt of the drug is released by 2 hours, about 25 to about 45% is released by 4 hours, about 55 to about 80% wt of the drug is released by 6 hours, and no less than 70% of the drug is released by 8 hours.

The release can also be such that no more than about 20% wt of the drug is released by 2 hours, about 20 to about 45% is released by 4 hours, about 55 to about 90% wt of the drug is released by 8 hours, and no less than 80% of the drug is released by 12 hours. The release can also be such that no more than about 20% wt of the drug is released by 2 hours, about 30 to about 60% is released by 4 hours, about 50 to about 70% wt of the drug is released by 6 hours, no less than 70% of the drug is released by 8 hours and no less than 80% of the drug is released by 12 hours. The release can also be such that no more than about 10% of the drug is released by 1 hour, no more than about 20% wt of the drug is released by 2 hours, about 30 to about 50% is released by 4 hours, about 40 to about 70% wt of the drug is released by 6 hours, no less than 60% of the drug is released by 8 hours and no less than 75% of the drug is released by 12 hours. The release can also be such that no more than about 10% of the drug is released by 1 hour, no more than about 20% wt of the drug is released by 2 hours, about 30 to about 50% is released by 4 hours, about 40 to about 70% wt of the drug is released by 6 hours, about 60% to about 85% of the drug is released by 8 hours and no less than 75% of the drug is released by 12 hours. The release can also be such that about 70 to about 95% wt of the drug is released by six hours, about 80 to about 100% of the drug is released by 8 hours, and no less than 90% of the drug is released by 12 hours, or wherein about 15 to about 35% wt of the drug is released by 2 hours, about 50 to about 85% is released by 4 hours, about 80 to about 100% of the drug is released by 8 hours, and no less than 90% of the drug is released by 12 hours after placement in an environment of use. The release can be such that less than 20% wt is released by about 1 hour, about 20-40% wt is released by about 2 hours, about 60-80% wt is released by about 4 hours, about 70-90% wt is released by about 6 hours, and at least 80% wt is released by about 8 hours after placement in an aqueous environment of use. The release can be such that less than 15% wt is released by about 1 hour, about 25-35% wt is released by about 2 hours, about 60-75% wt is released by about 4 hours, about 75-85% wt is released by about 6 hours, and at least about 90% wt is released by about 8 hours after placement in an aqueous environment of use. The release can be such that about 4-11% wt is released by about 1 hour, about 23-33% wt is released by about 2 hours, about 62-74% wt is released by about 4 hours, about 75-85% wt is released by about 6 hours, and at least about 90% wt is released by about 8 hours after placement in an aqueous environment of use.

Figure 5:
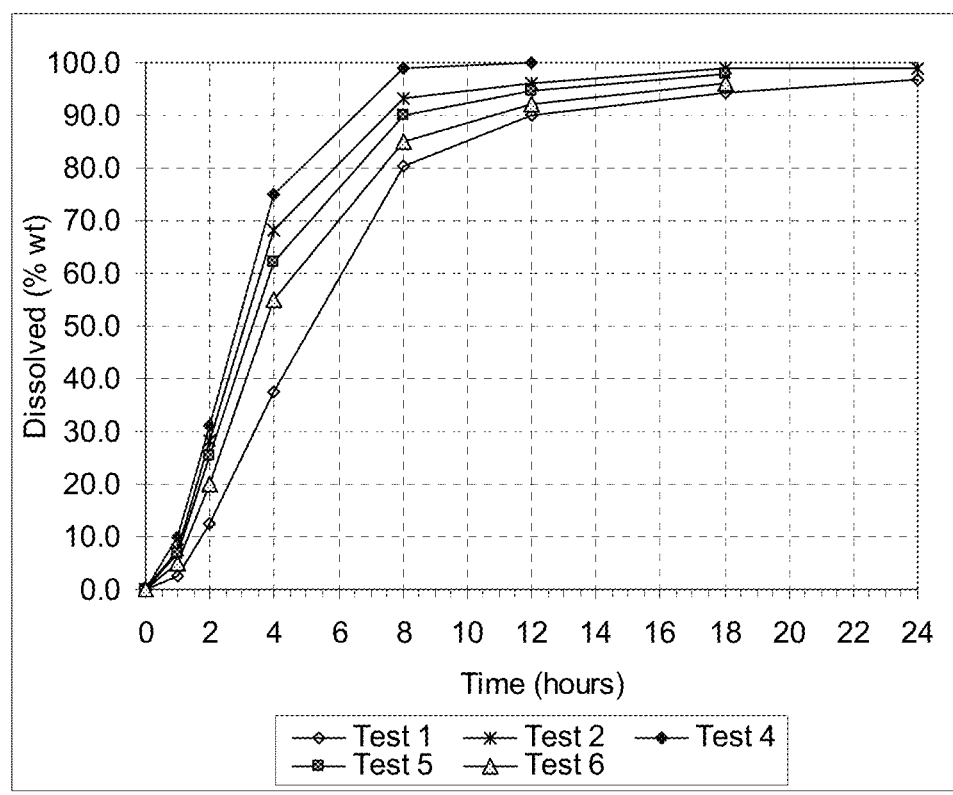
FIG. 5 depicts exemplary in vitro release profiles for controlled release dosage forms of the invention.
Figure 7:
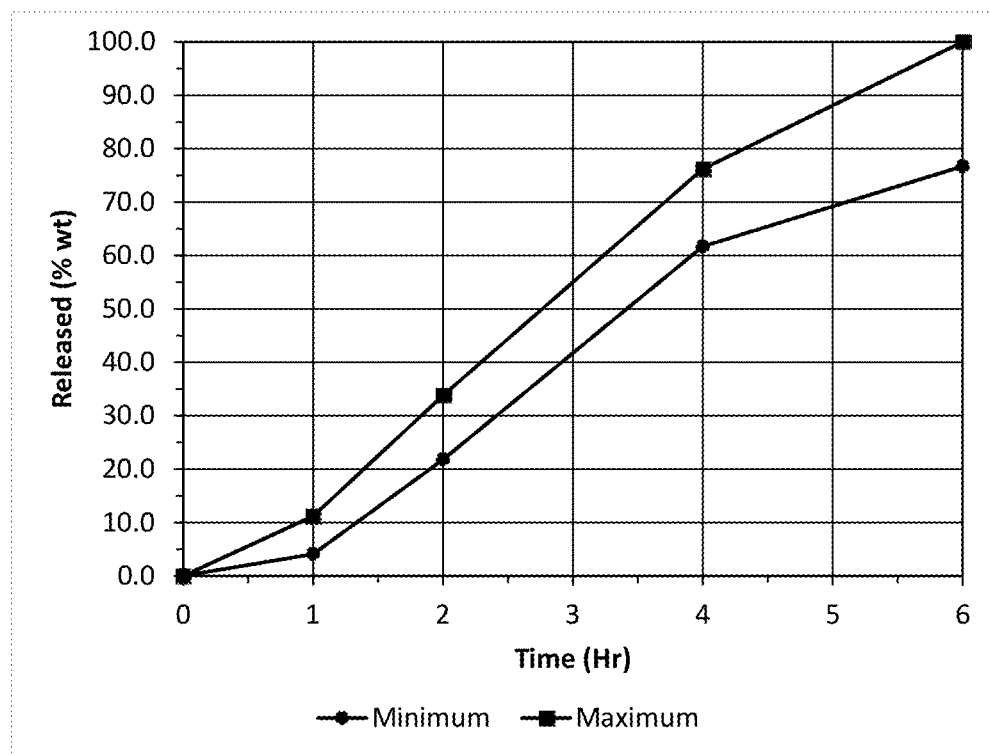
FIG. 7 depicts exemplary maximum and minimum in vitro release profiles following placement of the T2 dosage form in an aqueous environment of use.

FIGS. 1, 5, and 7 depict exemplary release profiles for release of drug from the core of the dosage form of the invention. FIG. 7 depicts a particular range of release profiles that can be provided by the T2 dosage form, wherein the range of release profiles is defined by and inclusive of the area between the maximum and minimum release profiles.

In some embodiments, the release profile is sigmoidal. In some embodiments, the release profile is first order or zero order. Drug is released in a continuous or controlled manner. In some embodiments, the dosage form of the invention excludes a gastroretentive dosage form. As used herein, a gastroretentive dosage form is an oral dosage form that following oral administration is designed to be retained in the stomach for a prolonged period of time and provides a majority of its sustained, controlled or extended drug release in the stomach.

The three phases of a sigmoidal release profile can be divided according to the weight percentage of drug, in a dosage form, that is released during each phase. In some embodiments, about 5-20% wt is released during the first phase, about 45-70% wt is release during the second phase and about 10-50% wt is released during the third phase. In some embodiments, about 5-15% wt is released during the first phase, about 55-70% wt is release during the second phase and about 15-45% wt is released during the third phase. In some embodiments, about 5-15% wt is released during the first phase, about 50-70% wt is release during the second phase and about 25-35% wt is released during the third phase. In some embodiments, the first phase lasts about 1 to 2 hours, the second phase lasts about 4 to 8 hours, and the third phase lasts about 2 hours or more. In some embodiments, the first phase lasts no more than about 2 hours, the second phase lasts about 4 to 8 hours, and the third phase lasts about 2 hours or more. In some embodiments, the first phase lasts no more than about 3 hours, the second phase lasts about 3 to 6 hours, and the third phase lasts about 1 hour or more. In some embodiments, the first phase lasts no more than about 2 hours, the second phase lasts about 3 to 6 hours, and the third phase lasts about 1 hour or more. In some embodiments, the first phase lasts no more than about 2 hours, the second phase lasts about 3 to 5 hours, and the third phase lasts about 1 hour or more.

Figure 2:
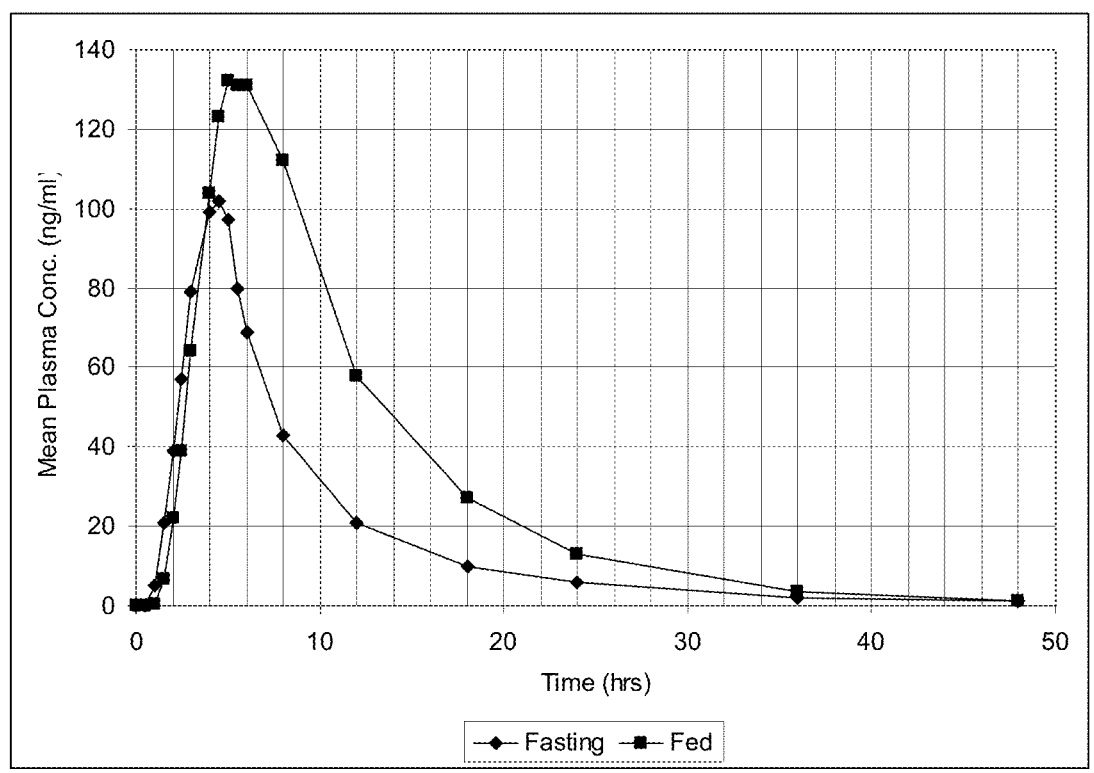
FIG. 2 depicts exemplary plasma profiles following oral administration of a controlled release device according to Example 1 (containing 20 mg of ARBAC) to subjects under fed (squares) and fasting conditions (diamonds).

The osmotic device provides an improved plasma profile (FIG. 2) when orally administered to a subject as compared to other related osmotic devices. The device unexpectedly exhibits a dramatic positive food effect contrary to the published literature on baclofen, which does not indicate the existence of a food effect upon the pharmacokinetic parameters of baclofen when administered orally. The device was orally administered in the fed and fasting states according to Example 4. It was determined that the instant osmotic device provides a substantial increase in Cmax, $AUC_{0-t}$ and $AUC_{0-inf}$ when administered in the fed state as compared to the fasting state. The table below summarizes the results for administration of an osmotic device containing 20 mg of ARBAC after a single dose.

TABLE 7

| | Mean values | |
|---|---|---|
| Parameter | Fed | Fasting |
| Tmax (hr) | about 5 (4-6) | about 4.5 (3.5-5.5) |
| Cmax (ng/ml) | about 155 (110-190) | about 120 (80-150) |
| $AUC_{0-t}$ (ng · h/ml) | about 1470 (1400-1900) | about 800 (550-1080) |
| $AUC_{0-inf}$ (ng · h/ml) | about 1490 (1400-1900) | about 830 (550-1080) |

Cmax increases by about 25-30%, $AUC_{0-t}$ increases by about 75-85% or about 80%, $AUC_{0-inf}$ increases by about 70-80% or about 75%, and Tmax increases by about 0.25 to about 0.75 hr or about 0.5 hr for the fed state administration over the fasting state administration.

The food effect continues to exist even after chronic dosing as demonstrated by steady state pharmacokinetics.

TABLE 8

| | Mean values | |
|---|---|---|
| Parameter | Fed | Fasting |
| $Tmax_{ss}$ (hr) | about 5 (4-6) | about 4.5 (3.5-5.5) |
| $Cmax_{ss}$ (ng/ml) | about 170 (120-220) | about 130 (80-150) |
| $Cmin_{ss}$ (ng/ml) | about 55 (10-100) | about 40 (5-80) |
| $AUC_{ss}$ (ng · h/ml) | about 1250 (1000-1700) | about 890 (600-1150) |

In another trial, the pharmacokinetic performance of the osmotic device was compared to that of an immediate release tablet of the same dosage strength when orally administered in the fasting state and steady-state multiple doses according to Example 5. It was determined that the instant osmotic device provides a substantial decrease in Cmax and AUC$_{0-12}$ and a substantial increase in Tmax as compared to the IR tablet. The table below summarizes the results.

TABLE 9

| Parameter | Mean values | |
|---|---|---|
| | Osmotic device (ARBAC) | IR tablet (rac-BAC) |
| Tmax (hr) (median or mean) | about 4 | about 1 |
| Cmin (ng/ml) | About 40 | About 90 |
| Cavg (ng/ml) | About 87 | About 174 |
| Cmax (ng/ml) | about 160 | about 336 |
| AUC$_{0-12}$ (ng · h/ml) | about 1040 | about 2080 |

The IR dosage form provides a higher Cmax and AUC than the osmotic device under fasting conditions and steady state following oral administration of multiple doses.

In yet another trial, the pharmacokinetic performance of the osmotic device was compared to that of an immediate release tablet of the same dosage strength when orally administered in the fasting state and single dose according to Example 6. It was determined that the instant osmotic device provides a substantial decrease in Cmax and AUC$_{0-12}$ and a substantial increase in Tmax as compared to the IR tablet. The table below summarizes the results.

TABLE 10

| | Osmotic device (10 mg ARBAC) T11 | Osmotic device (15 mg ARBAC) T12 | Osmotic device (20 mg ARBAC) T13 | IR tablet (20 mg rac-BAC) |
|---|---|---|---|---|
| Tmax (hr) (median or mean) | about 5 | about 4.5 | About 5 | about 1 |
| Cmax (ng/ml) | about 77 | about 100 | About 142 | about 425 |
| AUC$_{0-t}$ (ng · h/ml) | about 555 | about 680 | About 1060 | about 2300 |
| AUC$_{0-inf}$ (ng · h/ml) | About 575 | About 700 | About 1090 | About 2320 |

The IR dosage form provides a higher Cmax and AUC than the osmotic device under fasting conditions following oral administration of a single dose.

In some embodiments, the ER dosage form provides a Tmax of about 4 to about 7 hours, about 4 to about 5.5 hours, about 4 to about 5 hours, about 5 to about 7 hours or about 5 to about 6 hours after oral administration.

The extended release dosage form can provide reduced side effects (adverse events) compared to rapid release tablets containing racemic baclofen on an equimolar basis of arbaclofen. Example 7 details a study comparing the safety and efficacy of increasing doses of arbaclofen extended release tablets (AERT) of the invention, placebo and rapid release tablets containing racemic baclofen. AERT (10, 15 or 20 mg) are orally administered Q12h. Reference IR overencapsulated tablets of rac-BAC (10, 15 or 20 mg) are orally administered QID. Racemic baclofen is only 50% arbaclofen, so 10 mg of rac-baclofen is equal to 5 mg arbaclofen on a molar basis, and 10 mg of rac-baclofen QID is equal to 10 mg of arbaclofen BID on a molar basis. Of 354 randomized subjects, 59.0% had relapsing remitting and 36.7% had secondary progressive MS. The average baseline TNmAS score was 7.78. TNmAS and CGIC were statistically significant in favor of AERT group compared with placebo, while differences between AERT and baclofen were not statistically significant. MS Spasticity Scale (MSSS-88) showed a statistically significant improvement in AERT group compared with placebo. Epworth Sleepiness Scale (ESS) showed a statistically significant increase in sleepiness in the baclofen group, but not in the AERT group compared to placebo. Drowsiness and dizziness were less frequent in AERT group compared with baclofen. Even though the AERT provides substantially the same or better efficacy as the IR tablet, the AERT provides reduced sleepiness, drowsiness and/or dizziness.

The extended release (ER) dosage form exhibiting a positive food effect can be used to advantage in changing the current treatment of a subject undergoing rac-BAC or ARBAC therapy with other dosage forms not exhibiting a positive food effect. The subject's current treatment can be changed by reducing the dose of ARBAC administered while providing substantially the same or an improved clinical benefit when administering the ER dosage form with food. The subject's current treatment can also be changed by maintaining the same dose of ARBAC administered while providing an improved clinical benefit when administering the ER dosage form with food.

It has been determined that the plasma concentration of ARBAC is less critical than the concentration of ARBAC in CSF when treating spasticity, in particular spasticity associated with multiple sclerosis. The plasma concentration of ARBAC is substantially higher than the CSF concentration of ARBAC following administration of an ER dosage form of the invention. In some embodiments, the plasma concentration is at least 2-fold, at least 4-fold, at least 6-fold, at least 8-fold or at least 10-fold higher than the CSF concentration.

The invention provides a method of increasing the concentration of ARBAC in the CSF of a subject by administration of an ER dosage form of the invention. The method has two phases: a) a first phase during which a subject's concentration of ARBAC in CSF is increased to at least a minimum therapeutically effective concentration for a period of at least 12 hours or at least 16 hours; and b) a second phase during which a subject's concentration of ARBAC in CSF is maintained daily at or above the at least minimum therapeutically effective concentration for a period of at least 16 or at least 20 hours per day on a steady state basis during a treatment period. The first phase (the escalation phase) typically lasts 2-30 days, 2-21 days, 2-14 days, 2-7 days, 2-5 days or 2-3 days. The second phase (the maintenance phase) comprises the majority or the remainder of a subject's treatment period. As used herein, a treatment period is a period of time comprising plural dosing periods, and a dosing period is a period time from administration of one dose to administration of another. A treatment period is typically measured in days, weeks, months or years; whereas a dosing period is typically measured in hours. For example, BID administration is equivalent to two dosing periods in one day (or equivalent to one daily dosing period) in order to provide a total daily dose of drug. In some embodiments, the dosage form is administered once daily or twice daily.

In some embodiments, the invention provides a method of increasing the concentration of ARBAC in the cerebrospinal spinal fluid (CSF) of a subject, the method comprising: a) administering a first total daily dose of ARBAC or rac-BAC to the subject for a period of at least two days sufficient to achieve at least a minimum therapeutically effective concentration of ARBAC in the CSF for a period of at least 12 hours after administration; and b) chronically orally administering a second total daily dose of ARBAC in an extended release dosage form to the subject sufficient to maintain the at least minimum therapeutically effective concentration of ARBAC in the CSF for a period of at least 16 hours on a steady state basis.

The positive food effect can also be used to advantage when changing the current treatment method (protocol) of a subject undergoing treatment with ARBAC or rac-BAC. Since the ER dosage form provides at least the same clinical benefit at a substantially reduced dose of drug as compared to an IR dosage form containing rac-BAC, it can be used to reduce the amount of drug required to treat the subject. The invention provides a method of changing the current method of treatment of a subject undergoing daily treatment with one or more rac-BAC daily doses to a second method of treatment, the method comprising: a) determining the current daily dose of rac-BAC in the subject's current method of treatment; and b) indicating administration of a different dose of ARBAC in an extended release dosage form under fed conditions as the second method, wherein the different daily dose is less than the current daily dose. In its simplest embodiment, the invention can comprise merely substituting a subject's current IR dosage form of rac-BAC with an ER dosage of the invention comprising the same or a lower amount of ARBAC on a molar basis. In some embodiments, the subject's second method will include oral administration of the ER dosage form in the fed state.

The food effect can also be used to advantage to further control the absorption of ARBAC. For example, a subject can be orally administered a dose under fasting conditions and later a dose under fed conditions in a single day, or vice versa. For example, a subject could be administered the first dose with food and a second dose about 8 to 16 hours later. Fasting conditions are established by abstaining from consumption of food for at least 2, at least 3 or at least 4 hours before administration of a dose. The first and second doses and/or dosage forms can be the same or different. One or both dosage forms will exhibit a substantial positive food effect.

It is known that renally impaired subjects will typically experience drug accumulation, thereby causing higher Cmax and AUC values as compared to subjects with healthy renal functions. Accordingly, the doses described herein can be reduced further as needed for patients with impaired renal function. The level of dose reduction can be determined by a supervising clinician according to the subject's extent of renal impairment. Typically, the greater the impairment, the lower the dose required to provide therapeutically effective plasma levels of drug.

By "unitary core" is meant the core of an osmotic device that is not divided into two or more layers or laminas. The core is considered to be the composition enclosed within the wall, e.g. semipermeable membrane, of the osmotic device. The ingredients of the core may be present as a heterogeneous mixture or homogeneous mixture. A homogeneous mixture is one wherein all of the ingredients have been thoroughly mixed such that the composition of the formulation is substantially the same throughout different portions of the core. The combined step of mixing and directly compressing the ingredients of the core generally provides a homogeneous mixture. A heterogeneous mixture is one wherein the ingredients of the core are divided into two or more groups that are processed separately to form two or more respective blends, at least one of which contains drug and at least one of which contains the osmagent. The blends are then mixed together and compressed to form the unitary core. A heterogeneous mixture can be obtained by wet granulation, dry granulation, pelleting or combinations thereof. In some embodiments, wet granulation is preferred.

The terms "osmotic device" and "controlled release" or "extended release" dosage form are generally used herein interchangeably. An osmotic device is a controlled release device that comprises a semipermeable membrane surrounding the compressed drug-containing core, and optionally one or more other coatings and/or membranes. The preformed passageway, which is optional, is disposed at least through the semipermeable membrane. The membrane ruptures during use when the preformed passageway is absent.

The osmotic device can also comprise an inert water soluble or erodible coat composition surrounding the semipermeable membrane. The preformed passageway can be disposed through the inert water soluble or erodible coat composition and the semipermeable membrane or just through the semipermeable membrane.

FIG. 3 depicts a controlled release device (1) according to Example 1. The device comprises a core (2) surrounded by a semipermeable membrane (3) which includes a preformed passageway (4). Drug and osmopolymer (typically in gel form) exit through the passageway when the device is exposed to an aqueous environment of use. The device optionally comprises a drug-containing coat (5) exterior to the membrane (3). If the coat is placed onto the membrane after the preformed passageway has been formed in the membrane, then the coat plugs the passageway.

As used herein, the term "rupture" refers to breakage of the membrane such as by bursting, splitting, cracking, rending, severing, fracturing, tearing, cleaving, forcing open, puncturing, splitting, or ripping. The rupture occurs only to the extent that drug is still released from the core in a controlled release after rupture of the membrane. Rupture according to the invention excludes embodiments wherein the membrane breaks catastrophically thereby releasing the entire contents of the core in a burst or rapid manner. The mechanism of rupture, as used herein, is distinguished from mechanisms such as leaching, erosion or dissolution of material from the membrane, e.g. by inclusion of a pore-former in the membrane. The invention includes embodiments wherein the membrane ruptures even though it may also include a pore former.

One or more weakened regions can be included in the semipermeable membrane by: etching or scoring the membrane; shaping the osmotic device such that it has a shoulder, ridge, or border covered by the membrane and the membrane thickness at the shoulder, ridge or border is thinner than at a face adjacent the shoulder, ridge or border; including a brittling agent at one or more locations within or throughout the membrane; and/or applying the semipermeable membrane unevenly to the core or subcoat such that the membrane comprises one or more regions (weakened regions) that are thinner than the rest of the membrane, i.e. the membrane has a non-uniform thickness. One or more weakened regions can be independently located adjacent or spaced away from one or more preformed passageways. The membrane may comprise one or two preformed passageways and one or two weakened regions. The membrane will comprise at least one preformed passageway and at least one weakened region.

The present inventors have developed a process for forming weakened section(s) at one or more specific locations of a corresponding osmotic device. In some embodiments, the shape of the tablet includes one or more edges or shoulders or seams that create a weakened section the membrane during the film-forming process. The osmotic device (1) of FIG. 3 comprises two convex faces (made with concave punch; 6) circumferentially attached to a middle cylindrical section (7). Edges or shoulders (8) are formed at the areas where the faces (6) and cylindrical side (7) meet. The edges/shoulders comprise weakened sections, because the film formed at those locations is structurally compromised. FIG. 4A depicts an osmotic device (10) with flat faces (made with flat face punch), and FIG. 4B depicts an osmotic device (11) with concave faces (made with convex punch). As a result, increase in internal osmotic pressure ultimately causes rupture of one or more locations of the edges; however, it is necessary that the core comprise at least one water swellable excipient. Greater reproducibility and less variability is observed in the dissolution and plasma profiles of a batch of osmotic devices as compared to a batch of otherwise similar osmotic devices not having one or more edges, shoulders or seams. Other methods of forming an edge or seam on the surface of the osmotic device before application of the film-forming material are considered within the scope of the invention. In some embodiments, the shape of the tablet can be an ellipsoid of revolution or spheroid such that it does not comprise an edge or shoulder. The invention includes embodiments wherein the membrane does not rupture during use and embodiments wherein the membrane ruptures during use.

The examples disclose controlled release device formulations that differ in the composition of the core and semipermeable membrane.

The release profile of the osmotic device of the invention may vary from that shown in FIG. 1 according to the materials used to form the core and the semipermeable membrane covering the core, as well as the method used to form the passageway. The release profile can be influenced by the amount of excipient used to form the core, the type of excipient used to form the core, and the amount or type of any other material used to form the core such as osmotically effective solutes, osmopolymers, or osmagents. The release profile can also be influenced by the material used to form the semipermeable membrane, or by the material used to form any coating on the semipermeable membrane.

It should be understood that the device can assume any shape or form currently known in the art of osmotic devices. That is, the device may assume any different shape and/or size according to which are optimal for the intended environment of use. In some embodiments, its compressed core will comprise one or more shoulders, ridges or edges covered by the membrane. In particular embodiments, the shape and size of the device will be optimal for use in subject mammals such as animals or human beings. The device can also include surface markings, cuttings, grooves, letters and/or numerals for the purposes of decoration, identification and/or other purposes.

Osmotically effective solutes or osmotic agents, i.e. osmagents, that are capable of being totally or partially solubilized in the fluid, can be included in the core. These osmagents will aid in either the suspension or dissolution of the active agent in the core. Exemplary osmagents include organic and inorganic compounds such as osmotic salt, acid, base, chelating agent, halide salt, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. In some embodiments a halide salt is preferred. The osmagent can be present in concentrations ranging from about 5 to about 45% wt, about 10 to about 45% wt, about 15 to about 40% wt based upon the weight of the uncoated core.

These osmagents can also be incorporated to the core of the osmotic device to control the release of an active agent therein.

One or more osmopolymers (water swellable excipient(s), water swellable agent(s), water swellable polymer(s)) can also be added to the core of the device to aid in the delivery of the active agents. A "swellable agent" is any material that increases its volume upon exposure to a solution, such as a polymeric sorbent, for example, sodium polyacrylate, sodium polyacrylamide, poly-N-vinylpyrrolidone, poly-vinyltoluenesulfonate, poly-sulfoethyl acrylate, poly-2-hydroxyethyl acrylate, poly-vinylmethyloxazolidinone, hydrolyzed polyacrylamide, polyacrylic acid, copolymers of acrylamide and acrylic acid, and alkali metal salts of such of the polymers as contain sulfonate or carboxylate groups (see U.S. Pat. Nos. 3,926,891; 3,699,103, 5,693,411, all herein incorporated by reference in their entirety), or a naturally occurring water-swellable agent, such as mangrot seed, ground root of the buuk plant, cotton and sponge.

Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxyalkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, sodium carboxymethylcellulose, hydroxypropyl methylcellulose, polyethylene oxide, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, polyalkylene oxide (PAO) polymers, Polyox™ polyethylene oxide (PEO, which is a PAO) polymers having molecular weights of 100,000 to 5,000,000, starch graft copolymers, and Aqua-Keeps™ acrylate polymer polysaccharides.

In some embodiments, the core comprises two different water swellable polymers, wherein one polymer is present as a major portion and the other polymer is present as a minor portion of the total amount of water swellable polymer present. In some embodiments, the core comprises polyalkylene oxide (PAO) and hydroxyalkylcellulose derivative. In some embodiments, the PAO is present in a greater amount than the hydroxyalkylcellulose derivative. In some embodiments, the core comprises PEO and HPMC. In some embodiments, the PEO is present in a greater amount than the HPMC. In some embodiments, the weight ratio of PEO to HPMC in the core ranges from about 10:1 to about 25:1, about 12:1 to about 22:1, about 14:1 to about 25:1, about 14:1 to about 21:1, about 13:1 to about 17:1, about 15:1, about 17:1 to about 22:1, about 18:1 to about 20:1, or about 19:1.

One or more grades of PEO can be used as the swellable polymer(s) in the core. Suitable grades are listed below.

| POLYOX Grades | INCI Name | Approx. Molecular Weight | Viscosity (cPs) |
| --- | --- | --- | --- |
| POLYOX WSR N-10 | PEG-2M | 100,000 | 12-50a |
| POLYOX WSR N-80 | PEG-5M | 200,000 | 65-115a |
| POLYOX WSR N-750 | PEG-7M | 300,000 | 600-1,000a |
| POLYOX WSR N-3000 | PEG-14M | 400,000 | 2250-4500a |
| POLYOX WSR-205 | PEG-14M | 600,000 | 4500-8800a |
| POLYOX WSR N-12K | PEG-23M | 1,000,000 | 400-800b |
| POLYOX WSR N-60K | PEG-45M | 2,000,000 | 200-400b |
| POLYOX WSR-301 | PEG-90M | 4,000,000 | 1650-5500c |

In some embodiments, the PEO has a molecular of: about 4,000,000 or less, about 3,000,000 or less, about 2,000,000 or less, about 1,000,000 or less, about 1,000,000, about 600,000, about 400,000, about 300,000, about 200,000 or about 100,000. A combination of two or more grades of PEO can be used.

These materials swell or expand to an equilibrium state when exposed to water or other biological fluids. This volume expansion is used to physically force the pharmaceutical agent out through openings that have been formed in the wall, shell or coating during manufacture. A water insoluble or poorly water soluble active agent is primarily released as insoluble particles, which therefore have limited bioavailability. Exemplary osmopolymers are disclosed in U.S. Pat. Nos. 5,422,123; 4,783,337; 4,765,989; 4,612,008; 4,327,725; 4,609,374; 4,036,228; 4,992,278; 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in some embodiments, lightly cross-linked, such as cross-links being formed by covalent or ionic bonds.

In some embodiments, the core comprises at least one water swellable polymer and at least one osmagent. These excipients can be present in weight ratios of about 1.5:1 to about 1:1.5, about 1.25:1 to about 1:1.25, about 1.25:1 to about 1:1, about 1.2:1 to about 1:1, about 1.1:1 to about 0.7:1 to about 1:1, about 0.8:1 to about 1:1, about 0.85:1 to about 0.95:1, or about 0.9:1 based upon the total amount of water swellable polymer to the total amount of osmagent (osmotic salt).

Many common materials known by those of ordinary skill in the art are suitable for use as the semipermeable membrane. Exemplary materials include cellulose esters, cellulose ethers, cellulose esters-ethers and combinations thereof. However, it has been found that a semipermeable membrane consisting essentially of cellulose acetate (CA) and poly(ethylene glycol) (PEG) is particularly advantageous. In some embodiments, PEG 400, is preferred when used in combination with CA. This particular combination of CA and PEG provides a semipermeable membrane that gives the osmotic device a well controlled release profile for the active agent in the core and that retains its chemical and physical integrity in the environment of use. In some embodiments, the weight ratio of CA:PEG generally ranges from about 90-99% by weight of CA:about 10-1% by weight of PEG, and generally about 93-96% by weight of CA:about 7-4% by weight of PEG, or as otherwise described herein. The ratio can be varied to alter permeability and ultimately the release profile of the osmotic device.

Representative materials for making the semipermeable membrane include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a degree of substitution (D.S.) of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentalate, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876, 3,276,586, 3,541,005, 3,541,006, and 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride). These and others polymers are disclosed in U.S. Pat. Nos. 3,845,770, 3,916,899, 4,765,989 and 4,160,020; and in Handbook of Common Polymers (Scott, J. R. and Roff, W. J., eds.; 1971; CRC Press, Cleveland, Ohio).

The cellulose esters differ in their cellulose chain length and the type and amount of ester groups attached to the chain. For cellulose acetates, as the amount of acetyl content increases, the permeability decreases. The cellulose acetate grade 3 comprises 7-10% by weight of hydroxyl groups and has a viscosity of 200-280 seconds as determined by ASTM Method D 1343. The cellulose acetate grade 4 comprises 3-5% by weight of hydroxyl groups and has a viscosity of 6 to 45 seconds. The cellulose acetate grade 5 comprises 3-5% by weight of hydroxyl groups and has a viscosity of 100 to 240 seconds.

Some exemplary grades of cellulose acetate that are suitable for use in the making the semipermeable membrane are also described in the table below, which is included by way of example. Cellulose acetate of differing grades is readily available from Eastman Chemical Company (Kingsport, Tenn., USA).

| Cellulose Acetate | Hydroxyl Content (% by wt.) | Acetyl Content (% by wt.) | Viscosity* |
| --- | --- | --- | --- |
| Grade 1 | 8.7 | 32 | 2.4 P |
| Grade 2 | 3.5 | 39-40, 39.8 | 38 P |
| Grade 3 | 7-10 | 30-36 | 200-280 sec* |
| Grade 4 | 3-5 | 37-43 | 6-45 sec* |
| Grade 5 | 3-5 | 37-43 | 100-240 sec* |

*Viscosity determined as set forth in ASTM D817 (Formula A) and D1343, the disclosure of which is hereby incorporated by reference.

The above amounts are approximate (about) due to lot-to-lot manufacturing variations. Grade 1 can be considered a more narrowly defined Grade 3. Grade 2 can be considered a more narrowly defined Grade 5.

Films made from Polymer 1 (Grade 1, Grade 3 or a combination thereof) are considered to be more water permeable because of their relatively higher hydroxyl group content and relatively lower acetyl group content, and films made from Polymer 2 (Grade 2, Grade 4, Grade 5 or a combination thereof) are considered to be less water permeable because of their relatively lower hydroxyl group content and relatively higher acetyl group content. Films made from a combination of a more permeable grade (Polymer 1) and a less permeable grade (Polymer 2) will generally exhibit an intermediate water permeability falling between that of the two individual grades. For example, a film comprising a majority of more water permeable grade and a minority of less water permeable grade will generally exhibit a water permeability that is higher than a film comprising a minority of more water permeable grade and a majority of less water permeable grade and vice versa.

In some embodiments, the semipermeable membrane comprises at least two film-forming cellulose ester polymers. The polymers can be of two different grades but of the same type or of two different types. In some embodiments, the semipermeable membrane comprises a plasticizer (about 0.01 to about 10% wt) and the following two cellulose acetate (CA) polymers, wherein the weight percentage is based upon the weight of the membrane.

|  | I | II | III | IV | V |
|---|---|---|---|---|---|
| Polymer 1 (CA Grade 1 or 3) | 5-10 mg | 6-12 mg | 20-50% wt | 20-40% wt | 40-60% wt |
| Polymer 2 (CA Grade 2, 4 or 5) | 10-25 mg | 12-28 mg | 80-50% wt | 80-60% wt | 60-40% wt |

|  | VI | VII | VIII | XI | X |
|---|---|---|---|---|---|
| Polymer 1 (CA Grade 1 or 3) | 0-35 mg | 4-12 mg | 100-60% wt | 40-30% wt | 0-40% |
| Polymer 2 (CA Grade 2, 4 or 5) | 35-0 mg | 26-8 mg | 0-40% wt | 60-70% wt | 100-60% |

|  | XI | XII | XIII | XIV | XV |
|---|---|---|---|---|---|
| Polymer 1 (CA Grade 1 or 3) | 100-90% | 0-10% | 100-80% | 100-92% | |
| Polymer 2 (CA Grade 2, 4 or 5) | 0-10% | 100-90% | 0-20% | 0-8% | |

In some embodiments, the cellulose acetate present in the membrane comprises a majority of more water permeable grade (Polymer 1) and a minority of less water permeable grade (Polymer 2). In other embodiments, the cellulose acetate present in the membrane comprises a minority of more water permeable grade and a majority of less water permeable grade.

Plasticizers can be included in the semipermeable membrane to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly (ethylene glycol) Chemistry: Biotechnical and Biomedical Applications (J. M. Harris, Ed.; Plenum Press, NY) the disclosure of which is hereby incorporated by reference.

The plasticizer can be present in the following amounts or percentages, based upon the weight of the final dried membrane: 0.1-5 mg, 0.1-4 mg, 0.1-3 mg, 0.1-15% wt, 0.1-12.5% wt, 0.1-10% wt., 1-10% wt, 3 or −9% wt. or other ranges specified herein. The plasticizer can be PEG, esp. PEG 400, or as otherwise specified herein.

The optional inert polymer coat that covers the semipermeable membrane is made of synthetic, semisynthetic or natural material which, through selective dissolution and/or erosion shall allow the passageway to be unblocked thus allowing the process of osmotic delivery to start. The inert polymer coat will generally comprise an inert and non-toxic material which is at least partially, and generally substantially completely, soluble and/or erodible in an environment of use.

An optional drug-containing coat exterior to the semipermeable membrane may contain a second active agent that may or may not be the same as a first active agent in the core. The second active agent is available for immediate release. The second active agent can be applied to the surface of the device according to common methods of preparing similar osmotic devices such as applying to its surface solids in solution or suspension through the use of a sprayer that spreads them uniformly over the core or by employing nucleated compression or other suitable methods known to those of ordinary skill in the art. The external coat can comprise poly(vinylpyrrolidone) (PVP) and poly(ethylene glycol) (PEG) and can further comprise materials such as, by way of example and without limitation, hydroxypropyl methylcellulose (HPMC), hydroxyethylcellulose (HEC), sodium carboxymethyl-cellulose (CMC), dimethylamino-ethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat can also comprise dissolution aids, stability modifiers, and bioabsorption enhancers.

One or more grades of HPMC can be used as the water swellable polymer(s) and/or as the hydrophilic polymer in the core. Some suitable commercially available grades (hypromellose, METHOCEL E, METHOCEL K, METHOCEL A) are listed below.

| Grade | Methoxyl content (%) | Hydroxypropyl content (%) | Viscosity* (mPa-s) |
|---|---|---|---|
| METHOCEL E premium (group) | 28-30 | 7-12 | |
| METHOCEL E3 premium LV | 28-30 | 7-12 | 2.4-3.6 |
| METHOCEL E5 Premium LV | 28-30 | 7-12 | 4-6 |
| METHOCEL E6 premium LV | 28-30 | 7-12 | 4.8-7.2 |
| METHOCEL E15 premium LV | 28-30 | 7-12 | 12-18 |
| METHOCEL E50 premium LV | 28-30 | 7-12 | 40-60 |
| METHOCEL K premium (group) | 19-24 | 7-12 | |
| METHOCEL K3 premium LV | 19-24 | 7-12 | 2.4-3.6 cps |
| METHOCEL K4M | 19-24 | 7-12 | 2,663-4,970 |
| METHOCEL K15M | 19-24 | 7-12 | 13,275-24,780 |
| METHOCEL K100LV | 22-24 | 7-12 | 80-120 |
| METHOCEL K100M | 19-24 | 7-12 | 75,000-140,000 |
| METHOCEL F premium (group) | 27-30 | 4-7.5 | |
| Hypromellose type 1828 | 16.5-20.0 | 23.0-32.0 | |
| Hypromellose type 2208 | 19.0-24.0 | 4.0-12.0 | |
| Hypromellose type 2906 | 27.0-30.0 | 4.0-7.5 | |
| Hypromellose type 2910 | 28.0-30.0 | 7.0-12.0 | |
| METOLOSE 60SH (type 2910) | 28.0-30.0 | 7.0-12.0 | 50-10,000 |
| METOLOSE 65 SH (type 2906) | 27.0-30.0 | 4.0-7.5 | 50-4,000 |
| METOLOSE 90SH (type 2208) | 19.0-24.0 | 4.0-12.0 | 100-15,000 |
| METHOCEL A premium (group) | 27.5-31.5 | 0 | |
| METHOCEL A15 premium LV | 27.5-31.5 | 0 | 12-18 |
| METHOCEL A4C | 27.5-31.5 | 0 | 320-480 |
| METHOCEL A15C | 27.5-31.5 | 0 | 1,298-2,422 |
| METHOCEL A4M | 27.5-31.5 | 0 | 2,663-4,970 |
| METOLOSE SM | 27.5-31.5 | 0 | 32-5,600 |

Those of ordinary skill in the art will appreciate that the particular amount of second active agent employed will vary according to, among other things, the identity and physical properties and characteristics of the second active agent, the intended application of the osmotic device, the desired effect the second active agent is intended to have, and the physiological condition, if any, being treated. In some embodiments, the osmotic device excludes a drug-containing coat exterior to the semipermeable membrane.

As used herein, the term "preformed passageway" refers to a passageway or passageway precursor that has been formed on the semipermeable membrane of the device by mechanical means, such as by a laser, drill and/or etching apparatus. A preformed passageway is optionally plugged after initial formation, such as depicted in FIG. 3. The term "preformed passageway" is not intended to cover pores, holes, apertures, channels or other similar structures formed in the semipermeable membrane by incorporation of pore formers, water soluble particulates, or similar materials known to those of ordinary skill, into the semipermeable membrane of the rupturing controlled release device during manufacture of the osmotic device. Presence of the preformed passageway is optional.

The osmotic device of the invention optionally comprises at least one preformed passageway (pore, hole, or aperture) that communicates the exterior of the semipermeable membrane with the core of the device. The preformed passageway can be formed according to any of the known methods of forming passageways in a semipermeable membrane. Such methods include, for example, 1) drilling a hole through the semipermeable membrane with a bit or laser; 2) punching a hole through the semipermeable membrane; or 3) employing a tablet punch having a pin to punch a hole through the semipermeable membrane. The passageway can pass through the semipermeable membrane and one or more of any other coating onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming preformed passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., U.S. Pat. No. 3,845,770 to Theeuwes et al., PCT International Publication No. WO 04/103349 to Faour, and U.S. Pat. No. 6,809,288 to Faour, the disclosures of which are hereby incorporated by reference.

A preformed passageway can be made to substantially retain its size during use of the device or it can be made to increase in size during use of the dosage form. Preformed passageways of different sizes, shapes and functions can be used.

In some embodiments, the membrane defining the edge of the preformed passageway in the wall may tear (rupture) in a predetermined or random manner, and the shape of the preformed passageway after enlargement can be made to approximate a predetermined or randomly determined shape. The extent to which a passageway increases in size can also be related to the viscosity, molecular weight or degree of substitution of the at least one excipient. Generally, increasing the viscosity, molecular weight, or degree of substitution of the at least one excipient will increase the extent to which the passageway increases in size. In some embodiments, the edge of the membrane defining the preformed passageway in the wall does not tear during use of the osmotic device.

A device according to the present invention can optionally comprise one or more preformed passageways including two, three, four, five, six, seven, eight, nine, ten or more preformed passageways. It is only necessary that the preformed passageways, when present, together are adapted to permit controlled release of ingredients from the core during use. In some embodiments, the semipermeable membrane optionally comprises at least one preformed passageway having a diameter ranging from about 0.2 to about 0.8 mm, about 0.2 to about 0.6 mm, about 0.4 to about 0.8 mm, about 0.4 to about 0.6 mm, about 0.5 mm, about 0.7 mm, about 0.9 mm, about 1 mm. In other embodiments, the total area of the preformed passageway(s) present in the membrane ranges from 0.12 mm² to 2.1 mm². Preformed passageways of different sizes, shapes and functions can be employed.

The extent of rupture formation, i.e. the size of the rupture, can vary according to membrane thickness, membrane brittleness or flexibility, membrane composition, extent of swelling or expansion of the core during use, the thickness or weight of the subcoat. A thick membrane (0.3-1.5 mm) will generally rupture to a lesser extent than a thin membrane (0.075-0.29 mm). A brittle membrane will generally rupture to a greater extent than a flexible membrane. The more a core expands overall during use, the greater the extent of rupture overall. As the amount or weight of the subcoat increases, the overall or final rupture size decreases. After its initial formation in situ, the rupture can remain the same size or can increase in size during use. The formation of the rupture is abrupt; however, its subsequent increase in size can be gradual or intermittent.

Membrane thickness is related to membrane weight, i.e. the final weight of the membrane after preparation. Generally, the thicker the membrane, the heavier it is and the slower the release rate of drug. In some embodiments, a membrane weighing from 15 mg to 35 mg is applied to a core weighing from 100 mg to 300 mg. In some embodiments, the approximate membrane and core weights (based upon the weight of core without the membrane) are in any of the following ranges.

| Element | Weight (mg) | Weight (mg) | Weight (mg) | Weight (mg) | Weight (mg) | Weight (mg) |
|---|---|---|---|---|---|---|
| Core | 100-150 | 110-140 | 150-220 | 170-200 | 200-300 | 225-275 |
| Membrane | 15-30 or | 17-23 or 22-29 | 20-35 | 22-27 or 22-31 | 20-35 | 22-27 or 22-31 |

In some embodiments, the weight ratio of uncoated core to membrane applied to the core ranges from about 10:1 to about 15:1, about 11.5:1 to about 13:1, about 12.5:1, about 5:1 to about 10:1, about 6:1 to about 9:1, about 7:1 to about 9:1, or about 7:1 to about 8:1.

Particular embodiments of the improved AROS or AERT are described in Examples 1, 2, 9, 11 and 12. The T2 dosage form described in Examples 12 and 13 and other examples provides a particularly improved pharmacokinetic profile. Quite surprisingly, the T2 dosage form provides increased $AUC_{0\text{-}int}$ and Cmax and substantially later Tmax for arbaclofen as compared to the reference IR capsules. (FIG. 7) On the other hand, the T2 dosage form provides an earlier Tmax than the T1 and T3 dosage forms. Even though the T2 dosage form comprises the same amount of arbaclofen as the T1 and T3 dosage forms, it provides substantially higher Cmax and $AUC_{0\text{-}inf}$. This result is quite surprising. Apparently, the T2 dosage form is able to target a particular region of the upper GI tract resulting in substantially improved absorption of arbaclofen as compared to the IR capsules and the T1 and T3 dosage forms. Given that the T2 dosage form provides such high bioavailability, the dose of arbaclofen administered to a subject can be reduced as compared to administration of the IR dosage form. The T2 dosage form will still provide therapeutic efficacy and reduced adverse events albeit at a lower dose than the IR dosage form.

The invention provides a controlled or extended release dosage form of arbaclofen, wherein the dosage form exhibits a Tmax of less than 5 hours, or between about 3 to bout 5 hours, or between about 4 to about 5 hours, or between about 4.5 to about 5 hours, or about 4.8 hours.

Accordingly, the invention provides a controlled/extended release dosage form that provides improved bioabsorption (bioavailability) of ARBAC as compared to other controlled/extended release dosage forms on a dose equivalent basis. Improved bioabsorption is expressed as comparatively increased AUC, comparatively increased Cmax or both on a dose equivalent basis.

The osmotic device of the invention can also comprise adsorbents, antioxidants, buffering agents, colorants, flavorants, tablet antiadherents, tablet binders, tablet diluents, tablet fillers, tablet direct compression excipients, tablet glidants, tablet lubricants, tablet opaquants, colorant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene (BHT), hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "tablet binders" is intended to mean substances used to cause adhesion of powder particles in tablet granulations. Such compounds include, by way of example and without limitation, acacia, poly(vinylpyrrolidone), compressible sugar (e.g., NuTab™), ethylcellulose, gelatin, liquid glucose, povidone, copovidone (KOLLIDON® VA 64; BASF Group, Germany), pregelatinized starch, tragacanth, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, cellulosics in nonaqueous solvents, combinations thereof and other materials known to one of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

KOLLIDON® VA 64 (copovidone) is a vinylpyrrolidone-vinyl acetate copolymer that is soluble in water and alcohol. The monomers are present in an approximate molar ratio of 6:4. The copolymer has a molecular weight ranging from 45,000-70,000 as measured by laser light scattering in solution. Additional information can be obtained from BASF (www.pharma-ingredients.basf.com) or "Kollidon-Polyvinylpyrrolidone excipients for the Pharmaceutical Industry (BASF leaflet 03_030743e).

In some embodiments, the core comprises copovidone as binder present in an amount ranging from about 5% to about 15% wt, about 9% to about 13% wt, about 10 to about 12% wt or about 11% wt based upon the weight of the uncoated core. In some embodiments, the weight ratio of total water swellable polymer to total binder in the core ranges from about 6:1 to about 2:1, about 5:1 to about 3:1, about 3.5:1 to about 4.5:1, about 3:1 to about 4:1, about 4:1, about 5:1 to about 1:1, about 4:1 to about 1:1, about 3:1 to about 1:1, or about 2:1.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet diluents" or "tablet fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose (MCC), powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet opaquant" is intended to mean a compound used to render a tablet coating opaque. It may be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

It is contemplated that the osmotic device of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, glyceryl monostearate, PLURONIC® line (BASF), and the like; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, l-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butyleneglycoldimethacrylate, ethyleneglycol-dimethacrylate and methacrylate hydrogels.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Particular combinations of active agents that can be provided by the present controlled release device include: 1) a drug in the core from a first therapeutic class and a different drug in the external drug-containing coat from the same therapeutic class; 2) a drug in the core from a first therapeutic class and a different drug in the external drug-containing coat from a different therapeutic class; 3) a drug in the core having a first type of biological activity and a different drug in the external drug-containing coat having about the same biological activity; and/or 4) a drug in the core having a first type of biological activity and a different drug in the external drug-containing coat having a different second type of biological activity.

The therapeutic compound(s) contained within the present osmotic device can be formulated as its pharmaceutically acceptable salts. As used herein, "pharmaceutically acceptable salts" refer to derivatives of the disclosed compounds wherein the therapeutic compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. The pharmaceutically acceptable salts of the present invention can be synthesized from the parent therapeutic compound which contains a basic or acidic moiety by conventional chemical methods. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of therapeutic compound incorporated in each device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. In some embodiments, ARBAC is present at a dose strength of about 2.5 to about 50 mg, about 5 to about 15 mg, about 15 to about 25 mg, about 25 to about 50 mg, about 5 mg, about 10 mg, about 15 mg, about 20 mg, about 25 mg, about 30 mg, about 40 mg, about 50 mg, about 7.5 to about 12.5 mg, about 12.5 to about 17.5 mg, about 17.5 to about 22.5 mg, or about 22.5 to about 27.5 mg.

The term "unit dosage form" is used herein to mean a device containing a quantity of the drug, said quantity being such that one or more predetermined units may be provided as a single therapeutic administration.

If desired, the device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein. Printing may also be included in or on the dosage form.

The following examples should not be considered exhaustive, but merely illustrative of only a few of the many embodiments contemplated by the present invention. The methods described herein can be followed to prepare and use dosage forms and methods according to the invention.

Example 1

The following procedure is used to prepare a controlled release device containing $GABA_B$ receptor agonist as active ingredient (low, medium or high strength) in the core. The osmotic device tablets contain the following ingredients in the amounts indicated:

| Ingredient | Strength L | Strength M | Strength H | % wt | % wt |
|---|---|---|---|---|---|
| Core | | | | | |
| Active (mg) | >5-13 | 13-17 | 17-25 | 4-12 | 8 |
| Osmotic Agent (mg) | 40-60 | 60-80 | 80-110 | 30-45 | 36 |
| Filler (mg) | 4.5-7.5 | 7.5-10 | 10-15 | 3-7 | 4.6 |
| Binder (mg) | 10-17 | 17-24 | 24-35 | 5-15 | 11 |
| Swellable Polymer 1 (mg) | 2-3.1 | 3.1-4 | 4-8 | 0.1-5 | 2 |
| Swellable Polymer 2 (mg) | 40-60 | 60-80 | 80-110 | 30-45 | 38 |
| Antioxidant (mg) | 0.01-0.07 | 0.7-0.9 | 0.1-0.15 | 0.01-0.1 | 0.05 |
| Glidant (mg) | 0.2-0.3 | 0.3-0.4 | 0.4-0.7 | 0.01-0.5 | 0.2 |
| Lubricant (mg) | 0.2-0.3 | 0.3-0.4 | 0.4-0.7 | 0.01-0.5 | 0.2 |
| Core weight | 100-160 | 160-220 | 220-300 | | |
| Semipermeable membrane | | | | | |
| Rate film forming Polymer 1 (mg) | 5-10 | 5-12 | 5-12 | 20-50% | 20-40% |
| Rate film forming Polymer 2 (mg) | 10-25 | 12-28 | 12-28 | 80-50% | 80-60% |
| Plasticizer | 0.1-3 | 0.1-4 | 0.1-4 | 0.1-10% | 01-10% |
| Coating B (optional) | | | | | |
| Water soluble polymer with colorant | 3-5 | 5-7 | 7-9 | | |

The core composition is prepared by placing active ingredient, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores. Tabletting can be conducted using concave, convex or flat surface punches and dies. The compressed core can comprise one or more edges on the surface.

A first composition (semipermeable membrane) to cover the core is prepared as follows: two cellulose esters and a plasticizer are added to organic solvent and purified water, and mixed thoroughly to form a polymer solution. This solution is sprayed onto the tablets in a perforated pan coater to form film-coated cores. The cores will comprise one or more weakened sections along one or more edges.

A 0.25-1.5 mm hole is drilled through the coating to provide perforated film-coated tablets.

A finish coat (coating B) comprising Opadry and a colorant in purified water is applied onto the film-coated tablets to obtain the osmotic device tablets.

All different combinations of the core formulation and membrane formulation may be used. Exemplary osmotic devices of the above contain about 5 mg, about 10 mg, about 15 mg or about 20 mg of arbaclofen. The semipermeable membrane may or may not have a preformed passageway.

Example 2

The procedure of Example 1 is followed to prepare a controlled release device containing $GABA_B$ receptor agonist as active ingredient (low, medium or high strength) in the core. The osmotic device tablets contain the following ingredients in the amounts indicated:

| Ingredient | Strength 10 mg | Strength 15 mg | Strength 20 mg | % wt |
|---|---|---|---|---|
| Core | | | | |
| Active (mg) | About 10 | About 15 | About 20 | 4-12 |
| Osmotic Agent (mg) | 40-60 | 60-80 | 80-110 | 30-45 |
| Filler (mg) | 4.5-7.5 | 7.5-10 | 10-15 | 3-7 |
| Binder (mg) | 10-17 | 17-24 | 24-35 | 5-15 |
| Swellable Polymer 1 (mg) | 2-3.1 | 3.1-4 | 4-8 | 0.1-5 |
| Swellable Polymer 2 (mg) | 40-60 | 60-80 | 80-110 | 30-45 |
| Antioxidant (mg) | 0.01-0.07 | 0.7-0.9 | 0.1-0.15 | 0.01-0.1 |
| Glidant (mg) | 0.2-0.3 | 0.3-0.4 | 0.4-0.7 | 0.01-0.5 |
| Lubricant (mg) | 0.2-0.3 | 0.3-0.4 | 0.4-0.7 | 0.01-0.5 |
| Core weight | 100-160 | 160-220 | 220-300 | |
| Semipermeable membrane | | | | |
| Rate film forming Polymer 1 (mg) | 5-10 | 5-12 | 5-12 | 20-45% |
| Rate film forming Polymer 2 (mg) | 10-25 | 12-28 | 12-28 | 75-55% |
| Plasticizer | 0.1-3 | 0.1-4 | 0.1-4 | 0.1-10% |
| Coating B (optional) | | | | |
| Water soluble polymer with colorant | 3-5 | 5-7 | 7-9 | |

All different combinations of the core formulation and membrane formulation may be used. Exemplary osmotic devices of the above contain about 5 mg, about 10 mg, about 15 mg or about 20 mg of arbaclofen. The semipermeable membrane may or may not have a preformed passageway.

Example 3

The release (dissolution) profile for the exemplary dosage forms is determined according to one or more of the following methods. In some embodiments, U.S.P. method <711> entitled "Dissolution" is followed and any of the conditions below using Apparatus 1, 2, or 3 is followed.

USP Apparatus Type I dissolution (basket) at 100 rpm in purified water at 37°;

USP Apparatus Type II dissolution (paddles), in 900 ml of HCl 0.1N maintained at a temperature of 37±0.5° C.;

USP Apparatus Type II dissolution (paddles), first in 700 ml of HCl 0.1N maintained at a temperature of 37±0.5° C., during 1 hour, and then in 900 ml phosphate buffer pH 6 with 0.5-1% tween 80 or sodium lauryl sulfate;

USP Apparatus Type II dissolution (paddles), in 900 ml of HCl 0.1N at 50 rpm maintained at a temperature of 37±0.5° C.;

USP Apparatus Type II dissolution (paddles), in 900 ml of HCl 0.1N with 0.1% tween, maintained at a temperature of 37±0.5° C.;

USP Apparatus Type II dissolution (paddles), first in 900 ml of HCl 0.1N maintained at a temperature of 37±0.5° C., during 1 hour, and then the medium is adjusted to pH 6 with 1% tween;

USP Apparatus II dissolution with an ss helix sinker at 50 rpm in a volume of 900 ml of 0.001 N HCl;

USP Apparatus Type III dissolution (reciprocating cylinder), in distilled water (250 ml, 30 DPM at 37° C.).

Example 4

An osmotic device according to Example 1 or 2 was evaluated to determine its safety, tolerability and pharmacokinetic performance after administration of a single dose. The study was an open label, balanced, randomized, two-period, two-sequence, single oral dose, bioavailability study of Arbaclofen Extended Release Tablets (AERT), 20 mg in normal, healthy, adult human subjects under fasting and fed conditions, with a screening period of 28 days prior to the dosing in Period-I. In each study period, 18 blood samples (4 mL each), including pre-dose blood sample were collected from each subject to analyze the pharmacokinetic profile of the ARBAC. For efficacy evaluations, a total of 18 blood samples were collected in each period at the time points specified in the protocol. Standard non-compartmental pharmacokinetic parameters were derived for R-baclofen.

Safety was assessed from the screening period to the end of the study. It was assessed through physical examination, health status evaluation, vital signs assessment, 12-lead Electrocardiogram (ECG), Clinical laboratory parameters (e.g. biochemistry, hematology, immunology and urine analysis), pregnancy test (for female subjects), subjective symptomatology and monitoring of adverse events.

Dosing under fasting condition: After an overnight fast of at least 10 hours, a single oral dose of the test product (Arbaclofen Extended Release Tablets, 20 mg) was administered to the subjects with 240 mL of drinking water at ambient temperature in sitting posture.

Dosing under fed condition: After an overnight fast of at least 10 hours, the subjects were served high fat, high calorie meal, which they were required to consume within 30 minutes. A single oral dose of the test product (Arbaclofen Extended Release Tablets, 20 mg) was administered to the subjects at 30 minutes after serving the high fat meal. The dosage form was administered in sitting posture with 240 mL of drinking water at ambient temperature. The dosing activity was followed by a mouth and hands check to assess the compliance to dosing. The dosage form administration was as per the randomization schedule and under open label conditions.

Data from this study demonstrated that the test drugs were well tolerated. There were no deaths or serious AEs during the conduct of the study. There were no clinically significant findings in the vital signs assessment, ECG recording or the laboratory tests in any of the subjects. Pharmacokinetic results are summarized above.

Example 5

An Open Label, Balanced, Randomized, Two-Treatment, Two-Period, Two-Sequence, Cross-Over Bioavailability Study of Arbaclofen Extended Release Tablets, 20 mg (20 mg BID) Compared to the Plasma Profiles and Pharmacokinetic Parameters of Baclofen Tablets, USP, 20 mg (20 mg QID) After Multiple Dosing at Steady State in Healthy, Adult, Human Subjects Under Fasting Conditions.

The primary objective was to determine the relative bioavailability of the Test Product (T) (Arbaclofen Extended Release Tablets, 20 mg (20 mg BID)) compared to the Reference product (R) (Baclofen Tablets, USP, 20 mg (20 mg QID)), as measured by plasma profiles and pharmacokinetics parameters, after multiple dosing at steady-state in healthy, adult, human subjects under fasting conditions.

The secondary objective of the study was to evaluate the safety and tolerability at steady state after multiple dose administration of Arbaclofen ER Tablets, 20 mg BID in healthy, adult, human subjects under fasting condition.

The study was an open label, balanced, randomized, two-sequence, two-treatment, two-period, multiple dose, crossover, steady state oral bioavailability study in healthy, adult, human subjects under fasting conditions. In each study period, 24 blood samples (including 3 pre-dose samples on Day 3, 4 & 5 prior to the morning dose and 21 post-dose samples on Day 5), were collected from each subject except for the dismissed/discontinued subject and missing samples, to analyze the pharmacokinetic profile of the test as well as the reference drug.

Dosing Regimen for Test Product-T: A single oral dose (20 mg) of Test Product (T) was administered to the subjects with 240 mL of drinking water at ambient temperature in sitting posture. This activity was followed by mouth and hands check to ensure drug ingestion. The IMP administration was as per the randomization schedule and under open label conditions. The dosing was repeated every 12 hours for 5 days. On Day 5, only the morning dose was administered. Subjects received 9 tablets over 5 days (20 mg BID). For all morning doses, subjects fasted for a minimum of 8 hours pre-dose and 2 hours post-dose. For other doses, a minimum of 2 hours pre-dose and 1 hour post-dose fasting was required. Lunch was provided at 4.25 hours post-dose. Dinner and evening snack were provided at 8 hours and 13 hours post-dose, respectively. The dosing was repeated ever 12 hours for 5 days. On Day 5, only the morning dose was administered. Subjects received 9 tablets over 5 days (20 mg BID).

Dosing Regimen for Reference Product-R: A single oral dose (20 mg) of Reference Product (R) was administered to the subjects with 240 mL of drinking water at ambient temperature in sitting posture. This activity was followed by mouth and hands check to ensure drug ingestion. The dosage form administration was as per the randomization schedule and under open-label conditions. The dosing was repeated every 6 hours for 5 days. On Day 5, only the first two doses were administered. Subjects received 18 tablets over 5 days (20 mg QID). For all morning doses, subjects fasted for a minimum of 4 hours pre-dose and 2 hours post-dose. For other doses, a minimum of 2 hours pre-dose and 1 hour post-dose fasting was required. Lunch was provided at 3 hours post-dose. Dinner and evening snack were provided at 8 hours and 13 hours post-dose, respectively. The dosing was repeated every 6 hours for 5 days. On Day 5, only the first two doses were administered. Subjects received 18 tablets over 5 days (20 mg QID). A washout period of 07 days was maintained between the last dose in Period-I and the first dose in Period-II.

Data from this study demonstrated that the test and the reference drugs were well tolerated. There were no deaths or serious AEs during the conduct of the study. Pharmacokinetic results are summarized above.

Example 6

A Bioavailability Study of Arbaclofen Extended Release Tablets, 10 mg, 15 mg, 20 mg Compared to 20 mg Arbaclofen Solution Administered as a Single Dose Under Fasting Condition.

The purpose of this study was to determine the relative bioavailability of Arbaclofen Extended Release tablets 10 mg, 15 mg, and 20 mg compared to Arbaclofen Solution 20 mg in healthy, adult, human volunteers of both genders after a single dose under fasting conditions and to evaluate the safety and tolerability after single dose administration of Arbaclofen Extended Release Tablets 10 mg, 15 mg, and 20 mg in healthy human volunteers.

The study was an open label, balanced, randomized, four-periods four-sequence, single oral dose, crossover, bioavailability in normal, healthy, adult human subjects under fasting conditions, with a screening period of 28 days prior to the first dose administration. In each study period, 18 blood samples (4 mL each), were collected from each subject except for the dismissed subjects and missing sample, to analyze the pharmacokinetic profile of the test as well as the reference product After an overnight fast of at least 10 hours, the subjects were dosed with either of the compositions mentioned below. The administration was as per the randomization schedule and under open-label conditions.

Test Product (T11): 1 Arbaclofen Extended Release Tablet 10 mg with 240 mL of ambient temperature water. (Treatment dose=10 mg)

Test Product (T12): 1 Arbaclofen Extended Release Tablet 15 mg with 240 mL of ambient temperature water. (Treatment dose=15 mg)

Test Product (T13): 1 Arbaclofen Extended Release Tablet 20 mg with 240 mL of ambient temperature water. (Treatment dose=20 mg)

Reference Product (IR): 5 mL of Arbaclofen Solution, 20 mg/5 mL with 240 mL of ambient temperature water. (Treatment dose=20 mg)

Data from this study demonstrated that the test and the reference products were well tolerated. There were no deaths or serious AEs during the conduct of the study. Pharmacokinetic results are summarized above.

Example 7

A Randomized, Double-Blind, Parallel Group Study to Compare the Safety and Efficacy of Increasing Doses of Arbaclofen Extended Release Tablets (10, 15 or 20 mg BID) to Placebo and Baclofen Tablets, USP (10, 15 and 20 mg, QID) for the Treatment of Spasticity in Patients with Multiple Sclerosis.

Primary objectives include comparison of the efficacy of arbaclofen extended release tablets (AERT) to placebo on both the CGIC and the TNmAS across a range of doses and of the safety and tolerability of AERT to placebo over 12 weeks of treatment. Secondary objectives include comparison of AERT to Baclofen Tablets, USP across a range of doses based on; 1) efficacy as assessed by the TNmAS, CGIC, and MSSS-88 scales, and 2) safety as assessed by the DNRS, ESS, the rate of spontaneously reported somnolence and premature discontinuations due to AEs. Secondary objectives also include comparison of the efficacy of AERT 20 mg and 30 mg daily doses to placebo based on the TNmAS and CGIC scales. Abbreviations: a) MSSS-88—(88-item Multiple Sclerosis Spasticity Scale) assessment is not an evaluation of spasticity, but is intended to determine the effect spasticity has on the daily life of the subject; b) EDSS—(Expanded Disability Status Scale)—is a method of quantifying disability in multiple sclerosis and monitoring changes in the level of disability over time; c) LEMMT—(lower extremity manual muscle testing and rating scale)—a procedure for the evaluation of the function and strength of individual muscles and muscle groups based on effective performance of limb movement in relation to the forces of gravity and manual resistance; d) CGIC—(Clinical Global Impression of Change)—developed for use in NIMH-sponsored clinical trials to provide a brief, standalone assessment of the clinician's view of the subject's global functioning prior to and after initiating a study medication, and is used to measure the overall change in the subject's condition since starting the study; e) TNmAS—(total numeric-transformed modified Ashworth scale); f) DNRS (drowsiness numeric rating scale); and g) ESS (Epworth Sleepiness Scale).

This study compares the efficacy and safety of three (3) different AERT doses (20 mg/day, 30 mg/day and 40 mg/day) with Baclofen Tablets, USP (40 mg/day, 60 mg/day and 80 mg/day) and matching placebo over a 2-week period for each dose (lower, medium and higher), and over a 12-week maintenance period that begins at visit 5 and ends at visit 9 for the higher dose strengths.

Eligible subjects will be enrolled and undergo a two to four (2-4) week wash-out period for withdrawal of all medication used for anti-spasticity and/or muscle relaxation. If the subject is receiving disease-modifying medications, these must have been at a stable dose for at least three (3) months prior to screening, and the subject must be willing to maintain this treatment for the duration of the study. At visit 2, the baseline clinical evaluation is performed to confirm eligibility for study randomization. If subjects meet the randomization criteria, they will be assigned to one of the three treatment arms (AERT or Baclofen Tablets, USP or Placebo). During the first week of drug administration, subjects are up titrated to achieve the first (lower) therapeutic dose. The Dose Response Period begins after visit 3 during which subjects will remain for two (2) weeks at each dose of the two lower doses, having a clinical evaluation at the end of the corresponding phase and then, dose is increased for the following two (2) weeks (V4, V5 and V6) until the maximum dose is achieved. From V3 to V4 subject will stay at the lower therapeutic dose. From visit 4 to visit 5 subjects are increased to the intermediate therapeutic dose. Finally, from visit 5 to visit 6, subjects will receive the maximum therapeutic dose. After visit 6, the maximum dose is maintained for another ten (10) weeks (the Maintenance Phase) with two (2) visits (V7 and V8) resulting in a total of twelve (12) weeks treatment at the maximum therapeutic fixed dose. Finally, after the last clinical evaluation, visit 9, a two (2) week period for down titration and withdrawal from study medication is performed, followed by clinical follow-up (visit 10).

AERT (10, 15 or 20 mg) are orally administered Q12h. Reference IR over-encapsulated tablets of rac-BAC (10, 15 or 20 mg) are orally administered QID.

Results indicate the dosage forms of the invention are safe, well tolerated and efficacious. There were no deaths or serious AEs during the conduct of the study. Of 354 randomized subjects, 59.0% had relapsing remitting and 36.7% had secondary progressive MS. The average baseline TNmAS score was 7.78. TNmAS and CGIC were statistically significant in favor of AERT group compared with placebo, while differences between AERT and baclofen were not statistically significant. MS Spasticity Scale (MSSS-88) showed a statistically significant improvement in AERT group compared with placebo. Epworth Sleepiness Scale (ESS) showed a statistically significant increase in sleepiness in the baclofen group, but not in the AERT group compared to placebo. Drowsiness and dizziness were less frequent in AERT group compared with baclofen.

Example 8

A One Year, Open Label, Dose Escalation Study To Evaluate the Long-Term Safety of Arbaclofen Extended Release Tablets (AERT, 10, 15 or 20 mg tablets BID) in Multiple Sclerosis Subjects with Spasticity.

This is a multicenter, open-label, non-randomized dose escalation study in which the arbaclofen dose for each individual subject will be titrated up to the highest tolerated dose not exceeding 40 mg per day. Once this Maintenance Dose is achieved, each subject will be maintained on that dose for 1 year. All subjects will begin oral treatment with arbaclofen at 20 mg per day (2×10 mg) for two weeks, then increase to 30 mg per day (2×15 mg) for two weeks, and then increase to 40 mg per day (2×20 mg) based on Dose Escalation Criteria. Once the subject reaches the Maintenance Dose, they will remain on that dose for approximately 1 year. The Maintenance Dose is the highest tolerated dose, not to exceed 40 mg per day. During the course of the trial, the subject's health status may change so that the clinician and subject may wish to try a lower or higher dose of open-label AERT. Changes in the dose of AERT in response to changes in a subject's clinical status are permitted and will be documented in the CRF.

Results indicate the dosage forms of the invention are safe, well tolerated and efficacious. There were no deaths or serious AEs during the conduct of the study. The study enrolled 184 subjects, 63% were female, mean age was 48 years, average duration of MS diagnosis was 12 years, and mean baseline TNmAS score of 6.29. The most common adverse events (AEs) reported were muscle weakness (13%), somnolence (9.80%), dizziness (8.7%), incontinence (fecal 7.1%, urinary 6.5%), urgency (7.1%), pollakiuria (6.5%), asthenia (6%), and nausea (6%). AEs led to study discontinuation in 9.8% of subjects. No effects on laboratory parameters, vital signs, or ECGs were observed. TNmAS score decreased during the up-titration period, and remained consistent during the maintenance period. The improvement in spasticity was greater in subjects receiving 30 & 40 mg/day compared to 20 mg/day.

Example 9

The procedures Examples 1 or 2 are used to prepare a controlled release device containing $GABA_B$ receptor agonist as active ingredient in the core. The osmotic device tablets contain the following ingredients in the amounts indicated:

| Ingredient | % wt | % wt | % wt |
|---|---|---|---|
| Core | | | |
| Active | 4-12 | 6-11 | 7-10 |
| Osmotic Agent | 30-45 | 30-40 | 32-40 |
| Filler | 3-7 | 3.5-6.5 | 4-5 |
| Binder | 5-15 | 9-13 | 10-12 |
| Swellable Polymer 1 | 0.1-5 | 0.5-4 | 1-3 |
| Swellable Polymer 2 | 30-45 | 35-41 | 35-40 |
| Antioxidant | 0.01-0.1 | 0.01-0.1 | 0.01-0.1 |
| Glidant | 0.01-0.5 | 0.01-0.5 | 0.01-0.5 |
| Lubricant | 0.01-0.5 | 0.01-0.5 | 0.01-0.5 |
| Core weight | | | |
| Semipermeable membrane | | | |
| Rate film forming Polymer 1 | 20-50% | 20-40% | 25-30% |
| Rate film forming Polymer 2 | 80-50% | 80-60% | 70-60% |
| Plasticizer | 0.1-10% | 1-10% | 3-9% |

All different combinations of the core formulation and membrane formulation may be used. Exemplary osmotic devices of the above contain about 5 mg, about 10 mg, about 15 mg or about 20 mg of arbaclofen. The semipermeable membrane may or may not have a preformed passageway.

Example 10

BID methods of administering doses of $GABA_B$ receptor agonist in controlled/extended release dosage forms, wherein at least one of the dosage forms exhibits a positive food effect, are provided. This method is suitable for twice or thrice daily oral administration. Either one or both of the dosage forms may exhibit a positive food effect when administered with a high calorie-high fat meal.

Fasting

A subject fasts from food for a period of at least two hours, at least three hours or at least four hours and is then orally administered a dose of $GABA_B$ receptor agonist in a controlled/extended release dosage form exhibiting a positive food effect. The subject continues to fast for a period of at least one, at least 1.5, at least two or at least three hours after administration.

Fed

A subject is orally administered a dose of $GABA_B$ receptor agonist in a controlled/extended release dosage form exhibiting a positive food effect. The dose is administered: a) during a period of no more than about 2, no more than about 1.5, no more than about 1, no more than about 0.75, no more than about 0.5 or no more than about 0.25 hours before eating; or b) during a period of no more than 2, no more than 1.5, no more than 1, no more than 0.75, no more than 0.5 or no more than 0.25 hours after having eaten; or c) during the period in which the subject is eating.

Fed then Fasting

A subject is orally administered a dose according to the above "fed" method. After about 8 to about 16 hours, the subject is orally administered a dose according to the above "fasting" method. The subject may or may not eat one or more additional meals between the "fed" administration and the "fasting" administration.

Fasting then Fed

A subject is orally administered a dose according to the above "fasting" method. After about 8 to about 16 hours, the subject is orally administered a dose according to the above "fed" method. The subject may or may not eat one or more additional meals between the "fasting" administration and the "fed" administration.

Fed then Fed

A subject is orally administered a dose according to the above "fed" method. After about 8 to about 16 hours, the subject is orally administered a dose according to the above "fed" method. The subject may or may not eat one or more additional meals between the two "fed" administrations.

Fasting then Fasting

A subject is orally administered a dose according to the above "fasting" method. After about 8 to about 16 hours, the subject is orally administered a dose according to the above "fasting" method. The subject may or may not eat one or more additional meals between the two "fasting" administrations.

Example 11

A wet or dry granulation and compression method is followed to form the compressed core. A coating method is followed to form the membrane surrounding the core. The coated tablets so formed comprise the following ingredients in the amounts indicated:

| Ingredient | % wt | % wt | % wt | % wt | % wt | % wt |
|---|---|---|---|---|---|---|
| Core | | | | | | |
| ARBAC | 4-12 | 4-12 | 4-12 | 4-12 | 2-15 | 5-11 |
| NaCl or mannitol | 30-45 | 25-45 | 25-45 | 30-40 | 10-40 | 30-40 |
| MCC | 5-10 | 5-10 | 5-15 | 1-10 | 1-20 | 1-10 |
| Povidone or copovidone | 10-20 | 10-20 | 5-25 | 10-20 | 10-20 | 5-15 |
| Swellable HPMC | 0.5-5 | 0.5-5 | 0.1-7.5 | 1-5 | 1-5 | 2-7 |
| Swellable PEO | 25-50 | 25-50 | 25-50 | 25-40 | 25-35 | 30-45 |
| Optional Antioxidant | 0.01-0.5 | 0.01-0.5 | | | | |
| Optional Glidant | 0.01-0.5 | 0.01-0.5 | | | | |
| Optional Lubricant | 0.01-0.5 | 0.01-0.5 | | | | |
| Semipermeable membrane | | | | | | |
| Rate film forming Polymer 1 | 0-≤20 | 0-≤10 | 60-40 | 20-40 | 25-35 | |
| Rate film forming Polymer 2 | 100-≥80 | 100-≥90 | 40-60 | 60-80 | 60-70 | |
| Plasticizer | 0.1-10 | 0.1-10 | 0.1-10 | 0.1-10 | 0.1-10 | |

All different combinations of the core formulations and membrane formulations above can be used. Exemplary osmotic devices of the above contain about 5 mg, about 10 mg, about 15 mg or about 20 mg of arbaclofen. The semipermeable membrane may or may not have a preformed passageway.

Example 12

A wet or dry granulation and compression method is followed to form the compressed core. A coating method is followed to form the membrane surrounding the core. The coated tablets so formed comprise the following ingredients in the amounts indicated:

| Ingredient | % wt | T3 % wt | T2 % wt | T1 % wt |
|---|---|---|---|---|
| Core | | | | |
| ARBAC | 5-11 | 6-10 | 6-10 | 6-10 |
| NaCl | 30-40 | 33-39 | 33-39 | 33-39 |
| MCC | 2-8 | 3-6 | 3-6 | 3-6 |
| Copovidone | 6-16 | 9-13 | 9-13 | 9-13 |
| Swellable HPMC | 0.5-5 | 1-4 | 1-4 | 1-4 |
| Swellable PEO with MW ≤1,000,000 | 30-45 | 35-40 | 35-40 | 35-40 |
| Optional Antioxidant | 0.01-0.5 | 0.01-0.5 | 0.01-0.5 | 0.01-0.5 |
| Optional Glidant | 0.01-0.5 | 0.01-0.5 | 0.01-0.5 | 0.01-0.5 |
| Optional Lubricant | 0.01-0.5 | 0.01-0.5 | 0.01-0.5 | 0.01-0.5 |
| Semipermeable membrane | | | | |
| Cellulose acetate Grade 1 or 3 | 100-≥90 | | <100-≥90 | 20-35 |
| Cellulose acetate Grade 2, 4, or 5 | 0-<10 | <100-≥90 | 0-<10 | 60-80 |
| Plasticizer | 1-10 | | 1-10 | 1-10 |

The weight ratio of uncoated core to semipermeable membrane is about 9:1 to about 13:1 or about 10:1 to about 12.5:1.

The release can be such that about 60 to about 100% wt of the drug is released by about six hours, about 75 to about 100% of the drug is released by about 8 hours, and no less than 90% of the drug is released by about 10 hours after placement in an environment of use or after oral administration.

The release can also be such that about 45 to about 85% wt of the drug is released by six hours, about 65 to about 100% of the drug is released by 8 hours, and no less than 75% of the drug is released by 12 hours. The release can also be such that about 50 to about 85% wt of the drug is released by six hours, about 70 to about 100% of the drug is released by 8 hours, and no less than 85% of the drug is released by 10 hours. The release can also be such that about 5 to about 40% wt of the drug is released by 2 hours, 45 to about 85% wt of the drug is released by six hours, about 65 to about 100% of the drug is released by 8 hours, and no less than 75% of the drug is released by 12 hours.

The release can also be such that about 70 to about 95% wt of the drug is released by six hours, no less than about 80% wt of the drug is released by 8 hours, and no less than about 90% wt of the drug is released by 12 hours, or wherein about 15 to about 35% wt of the drug is released by 2 hours, about 50 to about 85% is released by 4 hours, about 80 to about 100% of the drug is released by 8 hours, and no less than 90% of the drug is released by 12 hours after placement in an environment of use. The release can be such that less than 20% wt is released by about 1 hour, about 20-40% wt is released by about 2 hours, about 60-80% wt is released by about 4 hours, about 70-90% wt is released by about 6 hours, and at least 80% wt is released by about 8 hours after placement in an aqueous environment of use. The release can be such that less than 15% wt is released by about 1 hour, about 25-35% wt is released by about 2 hours, about 60-75% wt is released by about 4 hours, about 75-85% wt is released by about 6 hours, and at least about 90% wt is released by about 8 hours after placement in an aqueous environment of use. The release can be such that about 4-11% wt is released by about 1 hour, about 23-33% wt is released by about 2 hours, about 62-74% wt is released by about 4 hours, about 75-85% wt is released by about 6 hours, and at least about 90% wt is released by about 8 hours after placement in an aqueous environment of use.

In vitro release profiles are determined as described herein.

Different combinations of the core formulations and membrane formulations in this or other examples can be used. Exemplary osmotic devices of the above contain about 5 mg, about 10 mg, about 15 mg or about 20 mg of arbaclofen. Other doses of ARBAC can be used. The semipermeable membrane may or may not have a preformed passageway.

Example 13

An open label, four period, four sequence, controlled, randomized single dose bioavailability study of ARBAC controlled release tablets (20 mg strength) versus equal dose of reference immediate/rapid release capsules (2×10 mg each) in healthy male and female volunteers under fasting conditions.

Figure 6:
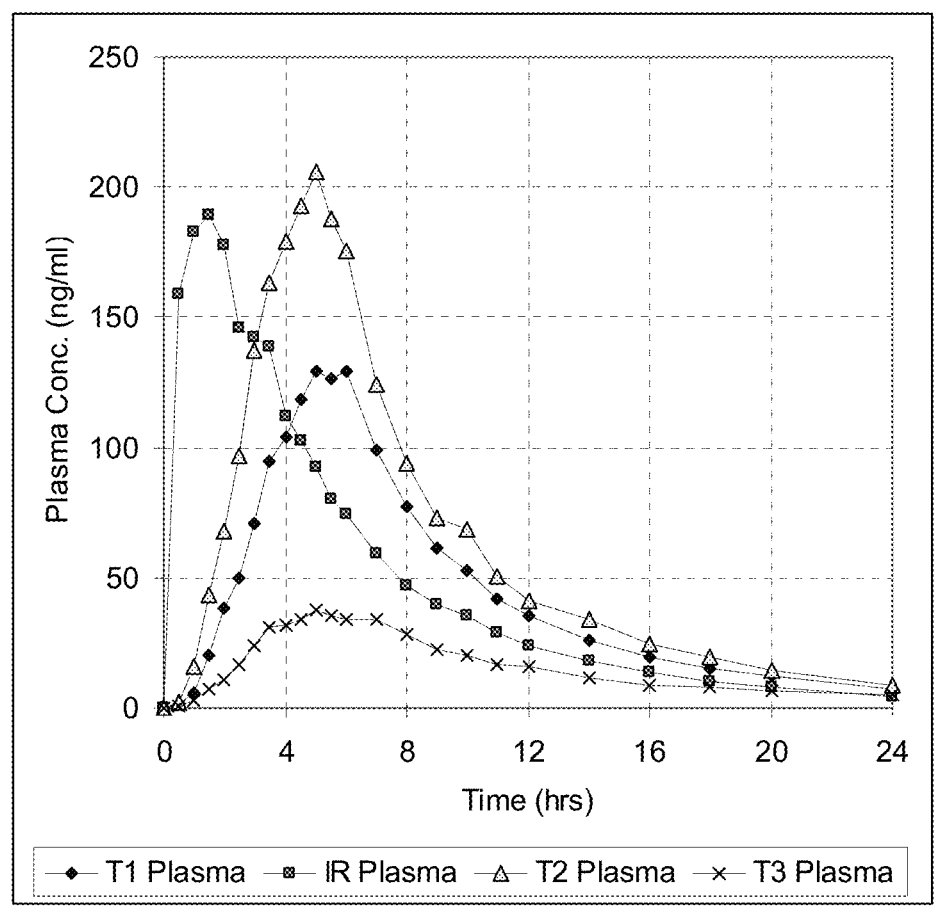
FIG. 6 depicts exemplary plasma profiles following oral administration of controlled release dosage forms (T1, T2, T3) and an immediate (rapid) release dosage form.

Three different controlled release formulations (T1, T2, T3) containing 20 mg of ARBAC each were prepared as described in Example 12. Their in vitro dissolution profiles were determined as described herein. Their pharmacokinetic performance (bioavailability, Cmax, AUC, Tmax, plasma profile) after a single dose in comparison to a reference IR capsule (2×10 mg of ARBAC each) was studied. Blood samples were obtained at regular time intervals over a 24-hour period. ARBAC content in blood was determined by HPLC-MS/MS. The following pharmacokinetic results were observed. The respective plasma profiles are depicted in FIG. 6.

T1 provided a mean Tmax of about 5.1 hrs, a mean Cmax of about 155 ng/ml, a mean $AUC_{0-t}$ of about 1030 ng*h/ml, a mean $AUC_{0-inf}$ of about 1145 ng*h/ml, and an MRT (mean residence time) of about 10.5 hrs.

T2 provided a mean Tmax of about 4.8 hrs, a mean Cmax of about 240 ng/ml, a mean $AUC_{0-t}$ of about 1460 ng*h/ml, a mean $AUC_{0-inf}$ of about 1560 ng*h/ml, and an MRT (mean residence time) of about 9.3 hrs.

T3 provided a mean Tmax of about 5.6 hrs, a mean Cmax of about 47 ng/ml, a mean $AUC_{0-t}$ of about 370 ng*h/ml, a mean $AUC_{0-inf}$ of about 530 ng*h/ml, and an MRT (mean residence time) of about 20.8 hrs.

The reference IR capsules provided a mean Tmax of about 1.4 hrs, a mean Cmax of about 220 ng/ml, a mean $AUC_{0-t}$ of about 1170 ng*h/ml, a mean $AUC_{0-inf}$ of about 1240 ng*h/ml, and an MRT (mean residence time) of about 6.8 hrs.

Example 14

An osmotic device containing arbaclofen is prepared using the methods described herein. The core of the osmotic device comprises arbaclofen, polyalkylene oxide, hydroxyalkyl alkylcellulose, MCC, NaCl and copovidone in the amounts or percentages described herein. The core optionally comprises antioxidant, tabletting glidant and tabletting lubricant. The semipermeable membrane comprises plasticizer, such as PEG, and one or two different grades of cellulose acetate film-forming polymer.

A wet or dry granulation and compression method is followed to form the compressed core. A coating method is followed to form the membrane surrounding the core. The coated tablets so formed comprise the following ingredients in the amounts indicated herein.

The percentages indicated for the core are with respect to the core. The percentages indicated for the membrane are with respect to the membrane.

All values disclosed herein may have standard technical measure error (standard deviation) of ±10%. The term "about" is intended to mean±10%, ±5%, ±2.5% or ±1% relative to a specified value, i.e. "about" 20% means 20±2%, 20±1%, 20±0.5% or 20±0.25%.

As used herein, the term "and/or", when used in a listing of items, is taken to mean that the invention includes embodiments of the listed items individually or in any combination thereof, i.e. is taken to mean "or a combination of any two or more of the above" or "a combination thereof". For example, the listing "a) . . . ; b) . . . ; and/or c) . . . " is taken to mean "a) . . . ; b) . . . ; c) . . . ; or d) a combination of any two or more of the above".

Due to intrasubject and intersubject variability in a population of test subjects, it should be understood that the pharmacokinetic results detailed herein may have a standard deviation of ±30%, ±20% or ±10%.

It should be noted that, unless otherwise specified, values herein concerning pharmacokinetic or dissolution parameters are typically representative of the mean or median values obtained from evaluation of at least 4, at least 8 or at least 12 of the same dosage forms.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating a condition that is therapeutically responsive to arbaclofen, the method comprising orally administering to a subject in need thereof a daily dose of arbaclofen in one or more extended release oral dosage forms comprising an active ingredient, wherein said active ingredient consists of arbaclofen (ARBAC), and wherein
   a) the dosage form provides an in vitro release profile for ARBAC as follows under conditions defined in USP <711> using a Type II apparatus with paddles in 0.1 N HCl at a temperature of 37±5° C.: about 70% wt to about 95% wt of the drug is released by six hours, no less than about 80% wt of the drug is released by 8 hours, and no less than about 90% wt of the drug is released by 12 hours, and
   b) the dosage form provides the following pharmacokinetic profile when a single dose comprising 20 mg ARBAC is administered orally to a subject: a mean Cmax of about 240 ng/ml±30%, and a mean $AUC_{0-t}$ of about 1460 ng*h/ml±30%.

2. The method of claim 1, wherein the daily dose is less than that which would be administered to the subject in an immediate release dosage form and wherein the one or more dosage forms of the invention are at least as therapeutically effective and provide less adverse events than the immediate release dosage form.

3. The method of claim 1, wherein the dosage form comprises:
   a) a core comprising the active ingredient, at least one water-swellable excipient, and at least one osmotic salt, and
   b) a membrane surrounding the core comprising at least one film-forming cellulose ester.

4. The method of claim 3, wherein the at least one water swellable excipient comprises a combination of at least one hydrophilic cellulose derivative and at least one polyalkylene oxide.

5. The method of claim 4, wherein the at least one water swellable excipient comprises by weight a majority of the at least one polyalkylene oxide polymer and a minority of the at least one hydrophilic cellulose derivative.

6. The method of claim 5, wherein the polyalkylene oxide polymer comprises poly(ethylene oxide), and the hydrophilic cellulose derivative comprises hydroxyalkyl alkylcellulose derivative or hydroxyalkylcellulose derivative.

7. The method of claim 4, wherein:
   the ratio of polyalkylene oxide to cellulose derivative is in the range of about 10:1 to about 25:1, about 13:1 to about 17:1 or about 17:1 to about 22:1;
   the weight ratio of uncoated core to membrane applied to the core ranges from about 10:1 to about 15:1 or about 5:1 to about 10:1; and/or
   the core further comprises at least one binder and the weight ratio of total water swellable polymer to total binder in the core ranges from about 6:1 to about 2:1 or about 5:1 to about 1:1.

8. The method of claim 3, wherein the at least one polyalkylene oxide has a molecular weight of about 1,000,000 or less.

9. The method of claim 3, wherein the membrane further comprises plasticizer, and the film-forming cellulose ester comprises a majority of a first grade of film-forming cellulose ester and a minority of a second grade of film-forming cellulose ester.

10. The method of claim 9, wherein the film-forming cellulose ester is cellulose acetate.

11. The method of claim 10, wherein the cellulose acetate is selected from any of the following grades:

| Cellulose Acetate | Hydroxyl Content (% by wt.) | Acetyl Content (% by wt.) | Viscosity* |
|---|---|---|---|
| Grade 1 | 8.7 | 32 | 2.4 P |
| Grade 2 | 3.5 | 39-40, 39.8 | 38 P |
| Grade 3 | 7-10 | 30-36 | 200-280 sec* |
| Grade 4 | 3-5 | 37-43 | 6-45 sec* |
| Grade 5 | 3-5 | 37-43 | 100-240 sec* | wherein the viscosity is determined as set forth in ASTM D817 (Formula A) or D1343.

12. The method of claim 11, wherein the cellulose acetate comprises, by weight, a majority of Grade 1, Grade 3 or a combination thereof, and a minority of Grade 2, Grade 4, Grade 5 or a combination thereof.

13. The method of claim 3, wherein the osmotic salt is present at a concentration ranging from about 5% wt to about 45% by weight based upon the weight of the uncoated core, or wherein the weight ratio of total water swellable polymer to osmotic salt is about 1.5:1 to about 1:1.5 or about 0.7:1 to about 1:1.

14. The method of claim 3, wherein the membrane ruptures from 0.1 to 1.5 hours after exposure of the device to an aqueous environment of use.

15. The method of claim 1, wherein the dosage form comprises a dose of 2.5 to 50 mg of ARBAC.

16. The method of claim 1, wherein the dosage form provides about the same or greater Cmax and about the same or greater AUC as compared to oral administration of a reference immediate release dosage form comprising the same dose of ARBAC.

17. The method of claim 1, wherein about 15% wt to about 35% wt of the drug is released by 2 hours, about 50% wt to about 85% wt is released by 4 hours, no less than about 80% wt of the drug is released by 8 hours, and no less than 90% wt of the drug is released by 12 hours after placement in an environment of use.

18. A method of treating a condition that is therapeutically responsive to arbaclofen, the method comprising orally administering to a subject in need thereof a daily dose of arbaclofen in one or more extended release oral dosage forms comprising about 2.5 to about 50 mg of arbaclofen (ARBAC) and made according to the following formulation:

| Ingredient | % wt |
| --- | --- |
| Core | |
| ARBAC | 5-11 |
| NaCl | 30-40 |
| MCC | 2-8 |
| Copovidone | 6-16 |
| Swellable HPMC | 0.5-5 |
| Swellable PEO with molecular weight ≤1,000,000 | 30-45 |
| Optional Antioxidant | 0.01-0.5 |
| Optional Glidant | 0.01-0.5 |
| Optional Lubricant | 0.01-0.5 |
| Semipermeable membrane | |
| Cellulose acetate Grade 2, 4, or 5 | 0-<10 |
| Cellulose acetate Grade 1 or 3 | 100-≥90 |
| Plasticizer | 1-10 | wherein about 15% wt to about 35% wt of the ARBAC is released by 2 hours, about 50% wt to about 85% wt is released by 4 hours, no less than about 80% wt of the drug is released by 8 hours, and no less than 90% wt of the drug is released by 12 hours after placement in an environment of use.

19. The method of claim 18, wherein the condition is spasticity.

20. The method of claim 1, wherein the dosage form, when administered in the fed state, exhibits a positive food effect in terms of an increased Cmax and AUC when comparing oral administration of the dosage form in the fed and fasting states.

21. The method of claim 1, wherein the extended release dosage form provides a plasma profile as described herein or as approximately depicted in FIG. 2 or FIG. 6.

22. The method of claim 1, wherein the extended release dosage form provides a dissolution profile as described herein or as approximately depicted in FIG. 1 or FIG. 5 inclusive of the area defined by minimum and maximum profiles.

23. The method of claim 1, wherein the pharmacokinetic profile is further defined as follows:
a mean Tmax of about 4.8 hrs±20%, a mean Cmax of about 240 ng/ml±30%, an $AUC_{0-t}$ of about 1460 ng*h/ml±30%, an $AUC_{0-inf}$ of about 1560 ng*h/ml±30%, and a mean residence time of about 9.3 hrs±30%.

24. The method of claim 1, wherein the dosage form provides a majority of drug release downstream of the stomach in the upper portion of the GI tract following oral administration thereof.

25. The method of claim 1, wherein the condition is spasticity.

26. The method of claim 1, wherein the subject being administered the controlled release dosage form experiences less drowsiness and/or less dizziness as compared to administration of a rapid release or immediate release dosage form containing an equimolar amount of arbaclofen present as racemic baclofen.

27. The method of claim 1, wherein the dosage form provides reduced adverse events as compared to administration of a rapid release or immediate release dosage form containing an equimolar amount of arbaclofen present as racemic baclofen.

28. A method of treating a condition that is therapeutically responsive to arbaclofen, the method comprising orally administering to a subject in need thereof a daily dose of arbaclofen in one or more extended release oral dosage forms, wherein following oral administration the dosage form provides a higher $AUC_{0-inf}$ and higher Cmax and a longer Tmax than that provided by an immediate release capsule containing the same amount of arbaclofen.

29. The method of claim 28, wherein the extended release dosage form exhibits in vitro dissolution profile approximating that described in FIG. 6 for formulation T2 and/or exhibits in vivo single dose plasma profile approximating that described in FIG. 7 inclusive of the area between the minimum and maximum.

30. The method of claim 28, wherein the condition is spasticity.

* * * * *